(12) United States Patent
Maeng et al.

(10) Patent No.: US 11,511,598 B2
(45) Date of Patent: Nov. 29, 2022

(54) APPARATUS AND METHOD FOR CONTROLLING AIR CONDITIONING OF VEHICLE

(71) Applicant: LG ELECTRONICS INC., Seoul (KR)

(72) Inventors: Ji Chan Maeng, Seoul (KR); Tae Hyun Kim, Seoul (KR); Beom Oh Kim, Suwon-si (KR)

(73) Assignee: LG ELECTRONICS INC., Seoul (KR)

( * ) Notice: Subject to any disclaimer, the term of this patent is extended or adjusted under 35 U.S.C. 154(b) by 537 days.

(21) Appl. No.: 16/664,449

(22) Filed: Oct. 25, 2019

(65) Prior Publication Data

US 2021/0078382 A1     Mar. 18, 2021

(30) Foreign Application Priority Data

Sep. 16, 2019    (KR) ........................ 10-2019-0113607

(51) Int. Cl.
    *B60H 1/00*          (2006.01)
    *G06N 3/02*          (2006.01)
    *A61B 5/01*          (2006.01)

(52) U.S. Cl.
    CPC ........... *B60H 1/00742* (2013.01); *A61B 5/01* (2013.01); *B60H 1/0073* (2019.05); *B60H 1/00814* (2013.01); *B60H 1/00871* (2013.01); *G06N 3/02* (2013.01)

(58) Field of Classification Search
    CPC ............ B60H 1/00828; B60H 1/00835; B60H 1/00864; B60H 1/00871
    USPC ..................................................... 454/69–165
    See application file for complete search history.

(56) References Cited

U.S. PATENT DOCUMENTS

| | | | |
|---|---|---|---|
| 11,318,811 B2 * | 5/2022 | Kusukame | F24F 11/62 |
| 2008/0248736 A1 * | 10/2008 | Aoki | B60H 1/00742 |
| | | | 454/75 |
| 2017/0330044 A1 * | 11/2017 | Telpaz | G05D 1/0088 |
| 2019/0009639 A1 * | 1/2019 | Ito | B60H 1/00871 |
| 2019/0084372 A1 * | 3/2019 | Gallagher | G05B 19/042 |
| 2019/0176730 A1 * | 6/2019 | Choi | B60H 1/00742 |
| 2019/0299744 A1 * | 10/2019 | Kusukame | B60K 28/06 |
| 2019/0322154 A1 * | 10/2019 | Ganguly | B60H 1/00742 |
| 2020/0156435 A1 * | 5/2020 | Patil | B60H 1/00742 |
| 2021/0031789 A1 * | 2/2021 | Mori | A61B 5/1114 |
| 2021/0078381 A1 * | 3/2021 | Rejkowski | B60H 1/00657 |

(Continued)

FOREIGN PATENT DOCUMENTS

| | | | |
|---|---|---|---|
| KR | 10-2009-0050434 A | | 5/2009 |
| KR | 10-2014-0001766 A | | 1/2014 |

*Primary Examiner* — Ko-Wei Lin
(74) *Attorney, Agent, or Firm* — Birch, Stewart, Kolasch & Birch, LLP

(57) ABSTRACT

Disclosed is a vehicle air conditioning control method which operates a vehicle air conditioning control apparatus by executing an artificial intelligence (AI) algorithm and/or a machine learning algorithm in a 5G environment connected for Internet of Things. The vehicle air conditioning control method includes acquiring a thermal image in a vehicle using an image sensor, acquiring thermal comfort information of each passenger in the vehicle using the thermal image, and controlling air conditioning of the vehicle based on the thermal comfort information of each passenger.

16 Claims, 18 Drawing Sheets

(56) References Cited

U.S. PATENT DOCUMENTS

2021/0206230 A1* 7/2021 Ishikawa ............ G06F 3/03547
2021/0331610 A1* 10/2021 Sakakibara ............ B60N 2/797

* cited by examiner

APPARATUS AND METHOD FOR CONTROLLING AIR CONDITIONING OF VEHICLE

CROSS-REFERENCE TO RELATED APPLICATION

This present application claims benefit of priority to Korean Patent Application No. 10-2019-0113607, entitled "APPARATUS AND METHOD FOR CONTROLLING AIR CONDITIONING OF VEHICLE," filed on Sep. 16, 2019, in the Korean Intellectual Property Office, the entire disclosure of which is incorporated herein by reference.

BACKGROUND

1. Technical Field

The present disclosure relates to an apparatus and a method for controlling air conditioning of a vehicle, and more particularly, to an apparatus and a method for controlling air conditioning of a vehicle which individually control the air conditioning for every passenger, based on thermal comfort information of each passenger in the vehicle.

2. Description of Related Art

An air conditioner for a vehicle is a device for cooling or heating the inside of a vehicle during a process of introducing air from the outside of the vehicle to the inside of the vehicle or circulating the air in the inside of the vehicle. Recently, air conditioners are mostly mounted in the vehicles so that drivers may drive under the pleasant environment. Further, vehicles include auto temperature controller (ATC) so that even though the user does not directly control the air conditioner, the air conditioning may be controlled by a specification optimized according to a usage environment.

Korean Patent Application Publication No. 10-2014-0001766 (published on Jan. 7, 2014; hereinafter referred to as "Related Art 1") discloses a technique for a vehicle interior temperature measuring method using a 3D thermal image in which a temperature of the interior of the vehicle including passengers is measured in the form of a thermal image by one pair of left and right stereo infrared sensors which are disposed in front of the indoor of the vehicle with a predetermined interval.

Korean Patent Application Publication No. 10-2009-0050434 (published on May 20, 2009; hereinafter referred to as "Related Art 2") discloses a technique for a method for generating, using, and displaying a thermal image for a sensing area using space temperature information measured by a thermal sensor which is used for a human body sensing function of the air conditioner.

That is, according to Related Arts 1 and 2, it is possible to efficiently perform the air conditioning by measuring a temperature of a sensing area or a passenger in the vehicle using a thermal image. However, according to Related Arts 1 and 2, when there is a plurality of users in the sensing area or in the vehicle, the air conditioning suitable for each user is not individually performed. Specifically, the user's satisfaction may be deteriorated due to personal taste of an actual user or an unexpected specific driving environment. Further, the air conditioner in the vehicle employs a method of collectively controlling a vehicle interior temperature so that it is difficult to provide a vehicle environment which satisfies all of the plurality of passengers having different personal tastes.

The above-described background technology is technical information that the inventors hold for the derivation of the present disclosure or that the inventors acquired in the process of deriving the present disclosure. Thus, the above-described background technology cannot be regarded as known technology disclosed to the general public prior to the filing of the present application.

SUMMARY OF THE INVENTION

An aspect of the present disclosure is directed to individually controlling the air conditioning corresponding to individual passengers based on thermal comfort information of individual passengers in the vehicle.

An aspect of the present disclosure is directed to solving the problem in that in a state in which personal thermal comfort is not considered, the air conditioning is performed for all passengers in the vehicle by the same way, which cannot satisfy the personal thermal comport.

An aspect of the present disclosure is directed to estimating the thermal comfort of each passenger by measuring a skin temperature of a distal part of the human body where many thermal sense cells are distributed to utilize for controlling the air conditioning.

An aspect of the present disclosure is directed to analyzing the thermal comfort by reflecting the vehicle information in consideration of the characteristic of the air conditioning control in the vehicle.

An aspect of the present disclosure is directed to dynamically controlling a direction of wind so that the wind is not concentrated in one place in the vehicle close to a discharge port through which the wind is discharged.

An aspect of the present disclosure is directed to preventing the discomfort caused by heat or cold due to excessive or insufficient air conditioning.

The object of the exemplary embodiment of the present disclosure is not limited to the above-mentioned objects and other objects and advantages of the present disclosure which have not been mentioned above may be understood by the following description and become more apparent from exemplary embodiments of the present disclosure. Furthermore, it will be understood that aspects and advantages of the present disclosure may be achieved by the means set forth in claims and combinations thereof.

The vehicle air conditioning control method according to an embodiment of the present disclosure may include: controlling individual air conditioning corresponding to each passenger based on thermal comfort information of each passenger in a vehicle.

According to an aspect of the present disclosure, a vehicle air conditioning control method includes: acquiring a thermal image in a vehicle using an image sensor; acquiring thermal comfort information of each passenger in the vehicle using the thermal image; and controlling air conditioning of the vehicle based on the thermal comfort information of each passenger.

According to the vehicle air conditioning control method of the embodiment of the present disclosure, the air conditioning is individually controlled based on thermal comfort which is different for every person, so that a state in which the thermal comfort is individually felt may be maintained.

Further, the acquiring of thermal comfort information of each passenger in the vehicle using the thermal image may include: recognizing a human body region of each passenger in the thermal image in the vehicle; analyzing a skin temperature feature using a temperature of the human body region; and extracting thermal comfort of each passenger based on a skin temperature feature analysis result.

The analyzing of a skin temperature feature using a temperature of the human body region may include extracting a skin temperature of a body part in accordance with expansion or contraction of the shunt vessel The analyzing of a skin temperature feature using a temperature of the human body region may include extracting a skin temperature based on a finger skin temperature and a skin temperature difference between a finger and a palm.

According to the embodiment of the present disclosure, by means of the acquiring of thermal comfort information of each passenger in the vehicle using the thermal image, the thermal comfort may be estimated by measuring a skin temperature of a distal part of the human body where many thermal sense cells are distributed so that whether the individual feels discomfort due to excessive or insufficient cooling or heating may be more accurately determined.

The extracting of thermal comfort of each passenger based on the skin temperature feature analysis result may include extracting thermal comfort of each passenger using at least one of thermal resistance information in accordance with a clothing wearing state of each passenger and temperature difference information in accordance with a seat position in the vehicle.

According to the embodiment of the present disclosure, by means of the extracting of thermal comfort of each passenger based on the skin temperature feature analysis result, the thermal comfort is analyzed in consideration of a thermal resistance of the clothing of the user and the thermal comfort is analyzed in consideration of the air state in the vehicle to improve the reliability of the product.

Further, the acquiring of thermal comfort information of each passenger in the vehicle using the thermal image may include: acquiring thermal comfort information of each passenger in the vehicle using one or more of a first deep neural network model and a second deep neural network model which are trained in advance to extract thermal comfort of the human body by analyzing a skin temperature feature, the first deep neural network model is a learning model which is trained to extract a skin temperature based on a finger skin temperature and a skin temperature difference between the finger and the palm and acquire the thermal comfort information of the human body based on the skin temperature, and the second deep neural network model is a learning model which is trained to extract a skin temperature based on at least one of thermal resistance information depending on the clothing wearing state of the passenger and temperature difference information in accordance with a position of a seat in the vehicle and acquire thermal comfort information of the human body based on the skin temperature.

According to the embodiment of the present disclosure, by means of the acquiring of thermal comfort information of each passenger in the vehicle using the thermal image, the thermal comfort information is acquired using a pre-trained deep neural network model and the vehicle air conditioning is performed based on the acquired thermal comfort information so that the performance of the vehicle air conditioning control system may be improved.

According to an embodiment of the present disclosure, the vehicle air conditioning control method may further include: acquiring vehicle information of a vehicle, and correcting thermal comfort information of each passenger in the vehicle acquired using the thermal image, based on the vehicle information of the vehicle. The vehicle information may include at least one of vehicle internal environment sensing information, vehicle external environment sensing information, and vehicle control sensing information.

The correcting of thermal comfort information of each passenger in the vehicle acquired using the thermal image, based on the vehicle information of the vehicle, may include correcting thermal comfort information of each passenger in the vehicle using a third deep neural network model trained in advance to extract a changed value of the thermal comfort information by analyzing the vehicle information of the vehicle, and the third deep neural network model may be a learning model trained to extract the changed value of the thermal comfort information of the human body based on at least one of vehicle internal environment sensing information, vehicle external environmental sensing information, and vehicle control sensing information and correct the thermal comfort information of the human body based on the changed value.

According to the embodiment of the present disclosure, by means of the correcting of thermal comfort information of each passenger in the vehicle acquired using the thermal image, based on the vehicle information of the vehicle, the thermal comfort is analyzed by reflecting vehicle information in consideration of the air conditioning control in the vehicle so that individual passengers in the vehicle maintain the pleasant state, thereby improving user's satisfaction of the product.

The controlling of air conditioning of the vehicle based on thermal comfort information of each passenger may include identifying a thermal comfort index calculated based on thermal comfort information of each passenger; detecting a passenger having a thermal comfort index which is equal to or lower than a reference value among passengers in the vehicle; figuring out an air conditioning discharging port located within a predetermined distance from the passenger having a thermal comfort index which is equal to or lower than a reference value; and adjusting a wind direction and a wind volume of the figured-out air conditioning discharging port.

The controlling of air conditioning of the vehicle based on thermal comfort information of each passenger may include adjusting a wind direction by controlling a discharging angle using a wind direction adjusting motor equipped in an air conditioning discharging port, and adjusting a wind volume by calculating a target duty ratio by performing PID control (e.g., proportional-integral-derivative control) and transmitting the calculated target duty ratio to a wind volume adjusting motor, the adjusting of a wind volume may include calculating a gain value corresponding to thermal comfort and using the calculated gain value as a gain value for PID control.

According to the embodiment of the present disclosure, by means of the controlling of air conditioning of the vehicle based on thermal comfort information of each passenger, a wind discharging direction is dynamically adjusted such that the wind discharged through an air conditioning discharging port is not concentrated to a face or a back of a hand, thereby improving user's satisfaction based on the thermal comfort.

According to another aspect of the present disclosure, a vehicle air conditioning control apparatus includes a thermal image acquirer configured to acquire a thermal image in a vehicle using an image sensor; a thermal comfort acquirer configured to acquire thermal comfort information of each passenger in the vehicle using the thermal image; and a controller configured to control air conditioning of the vehicle based on thermal comfort information of each passenger.

The thermal comfort acquirer may include: a human body recognizer configured to recognize a human body region of each passenger in the thermal image in the vehicle; an analyzer configured to analyze a skin temperature feature using a temperature of the human body region; and an extractor configured to extract thermal comfort of each passenger based on the skin temperature feature analysis result.

According to the embodiment of the present disclosure, by means of the vehicle air conditioning control apparatus, the air conditioning is individually controlled for every passenger based on thermal comfort information of each passenger in the vehicle so that it is possible to maintain the state in which the thermal comfort may be felt by individuals by focusing the thermal comfort of the passenger rather than a temperature in the vehicle.

The analyzer may extract a skin temperature of a body part in accordance with expansion or contraction of the shunt vessel.

The analyzer may extract a skin temperature based on a finger skin temperature and a skin temperature difference between a finger and a palm.

According to the embodiment of the present disclosure, by means of the analyzer, the thermal comfort is estimated by measuring a skin temperature of a distal part of the human body where many thermal sense cells are distributed so that whether to individually feel discomfort due to excessive or insufficient cooling or heating may be more accurately determined.

The extractor may extract thermal comfort of each passenger using at least one of thermal resistance information in accordance with a clothing wearing state of each passenger and temperature difference information in accordance with a seat position in the vehicle.

According to the embodiment of the present disclosure, by means of the extractor, the thermal comfort is analyzed in consideration of a thermal resistance of the clothing of the user and the thermal comfort is analyzed in consideration of the air state in the vehicle to improve the reliability and the performance of the product.

The thermal comfort acquirer acquires thermal comfort information of each passenger in the vehicle using one or more of a first deep neural network model and a second deep neural network model which are trained in advance to extract thermal comfort of the human body by analyzing a skin temperature feature, the first deep neural network model is a learning model which is trained to extract a skin temperature based on a finger skin temperature and a skin temperature difference between the finger and the palm and acquire the thermal comfort information of the human body based on the skin temperature, and the second deep neural network model is a learning model trained to extract a skin temperature based on at least one of thermal resistance information depending on the clothing wearing state of the passenger and temperature difference information in accordance with a position of a seat in the vehicle and acquire thermal comfort information of the human body based on the skin temperature.

According to the embodiment of the present disclosure, by means of the thermal comfort acquirer, the thermal comfort information is acquired using a pre-trained deep neural network model and the vehicle air conditioning is performed based on the acquired thermal comfort information so that the performance of the vehicle air conditioning control system may be improved.

According to an embodiment of the present disclosure, the vehicle air conditioning control apparatus may further include: a vehicle information acquirer configured to acquire vehicle information of a vehicle and a thermal comfort corrector configured to correct thermal comfort information of each passenger in the vehicle acquired using the thermal image, based on the vehicle information of the vehicle, and the vehicle information may include at least one of vehicle internal environment sensing information, vehicle external environment sensing information, and vehicle control sensing information.

The thermal comfort corrector corrects thermal comfort information of each passenger in the vehicle using a third deep neural network model trained in advance to extract a changed value of the thermal comfort information by analyzing the vehicle information of the vehicle, and the third deep neural network model may be a learning model trained to extract the changed value of the thermal comfort information of the human body based on at least one of vehicle internal environment sensing information, vehicle external environmental sensing information, and vehicle control sensing information and correct the thermal comfort information of the human body based on the changed value.

According to the embodiment of the present disclosure, by means of the thermal comfort corrector, the thermal comfort is analyzed by reflecting vehicle information in consideration of the air conditioning control in the vehicle so that individual passengers in the vehicle maintain the pleasant state, thereby improving user's satisfaction of the product.

Further, the controller detects a passenger having the calculated thermal comfort index which is equal to or lower than a reference value among passengers in the vehicle based on the thermal comfort information of each passenger in the vehicle, figures out an air conditioning discharging port located within a predetermined distance from the passenger having a thermal comfort index which is equal to or lower than a reference value; and adjusts a wind direction and a wind volume of the figured-out air conditioning discharging port.

Further, the controller adjusts a wind direction by controlling a discharging angle using a wind direction adjusting motor equipped in an air conditioning discharging port, adjusts a wind volume by calculating a target duty ratio by performing PID control and transmitting the calculated target duty ratio to a wind volume adjusting motor, and calculates a gain value corresponding to thermal comfort information and uses the calculated gain value as a gain value for PID control, thereby adjusting the wind volume.

According to the embodiment of the present disclosure, by means of the controller, the air conditioning control of the vehicle is performed not only by selection of the user, but a wind discharging direction is dynamically adjusted such that the wind discharged through an air conditioning discharging port is not concentrated to a face or a back of a hand, thereby improving user's satisfaction based on the thermal comfort.

In addition, in order to implement the present disclosure, there may be further provided other methods, other systems, and a computer-readable recording medium having a computer program stored thereon to execute the methods.

Other aspects and features as well as those described above will become clear from the accompanying drawings, claims, and the detailed description of the present disclosure.

According to the embodiment of the present disclosure, the air conditioning is individually controlled for every passenger based on thermal comfort information of each passenger in the vehicle so that it is possible to maintain the state in which the thermal comfort may be individually felt by focusing the thermal comfort of the passenger rather than a temperature in the vehicle.

Further, the thermal comfort is estimated by measuring a skin temperature of a distal part of the human body where many thermal sense cells are distributed so that whether to individually feel discomfort due to excessive or insufficient cooling or heating may be more accurately determined.

Further, the thermal comfort is analyzed in consideration of a thermal resistance of the clothing of the user and the thermal comfort is analyzed in consideration of the air state in the vehicle to improve the reliability and the performance of the product.

Further, the thermal comfort information is acquired using a pre-trained deep neural network model and the vehicle air conditioning is performed based on the acquired thermal comfort information so that the performance of the vehicle air conditioning control system may be improved.

Further, the thermal comfort is analyzed by reflecting vehicle information in consideration of the air conditioning control in the vehicle so that individual passengers in the vehicle maintain the pleasant state, thereby improving user's satisfaction of the product.

Further, the air conditioning of the vehicle is controlled not only by selection of the user, but a wind discharging direction is dynamically adjusted such that the wind discharged through an air conditioning discharging port is not concentrated to a face or a back of a hand, thereby improving user's satisfaction based on the thermal comfort.

Further, the vehicle air conditioning is controlled through a 5G network-based communication so that the data processing may be quickly performed, thereby further improving the performance of a vehicle air conditioning control system.

Further, even though the vehicle air conditioning control apparatus itself is a mass-produced uniform product, the user recognizes the vehicle air conditioning control apparatus as a personalized device, so that an effect as a user-customized product may be achieved.

The effects of the present disclosure are not limited to those mentioned above, and other effects not mentioned can be clearly understood by those skilled in the art from the following description.

BRIEF DESCRIPTION OF THE DRAWINGS

The above and other aspects, features, and advantages of the present disclosure will become apparent from the detailed description of the following aspects in conjunction with the accompanying drawings, in which.

DETAILED DESCRIPTION

Figure 1:
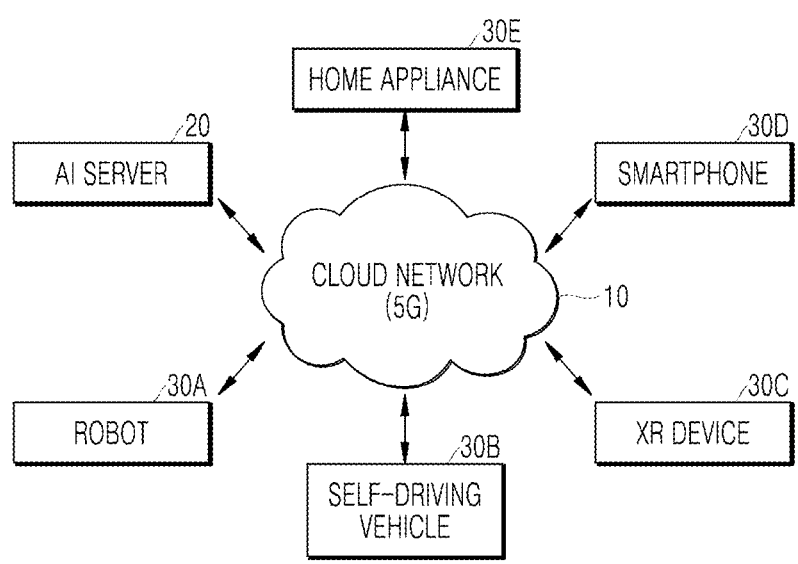
FIG. 1 is an exemplary diagram of an AI system-based vehicle air conditioning control environment including an AI server, a self-driving vehicle, a robot, an XR device (e.g., extended reality), a user terminal, or a home appliance, and a cloud network connecting one or more of these components to each other, according to an embodiment of the present disclosure.

The advantages and features of the present disclosure and ways to achieve them will be apparent by making reference to embodiments as described below in detail in conjunction with the accompanying drawings. However, the description of particular example embodiments is not intended to limit the present disclosure to the particular example embodiments disclosed herein, but on the contrary, it should be understood that the present disclosure is to cover all modifications, equivalents and alternatives falling within the spirit and scope of the present disclosure. The example embodiments disclosed below are provided so that the present disclosure will be thorough and complete, and also to provide a more complete understanding of the scope of the present disclosure to those of ordinary skill in the art. In the interest of clarity, not all details of the relevant art are described in detail in the present specification in so much as such details are not necessary to obtain a complete understanding of the present disclosure.

The terminology used herein is used for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. Furthermore, these terms such as "first," "second," and other numerical terms, are used only to distinguish one element from another element. These terms are generally only used to distinguish one element from another.

A vehicle described herein may be a concept including an automobile and a motorcycle. In the following, the vehicle will be described mainly as an automobile.

The vehicle described in the present disclosure may include, but is not limited to, a vehicle having an internal combustion engine as a power source, a hybrid vehicle having an engine and an electric motor as a power source, and an electric vehicle having an electric motor as a power source.

Further, the air conditioner described in the present specification is a device having a function of controlling a state of the air in the vehicle. A cooling-only device, called as an air conditioner is included in the scope of the air conditioner according to the embodiment of the present disclosure and a heat pump which is capable of cooling and heating and also has a hot water supplying function depending on the equipment may also be included in the scope of the air conditioner according to the embodiment of the present disclosure.

Hereinafter, embodiments of the present disclosure will be described in detail with reference to the accompanying drawings. Like reference numerals designate like elements throughout the specification, and overlapping descriptions of the elements will not be provided.

FIG. 1 is an exemplary view of an AI system-based vehicle air conditioning control environment including an AI server, a self-driving vehicle, a robot, an XR device, a user terminal or a home appliance, and a cloud network connecting one or more of these components to each other, according to an embodiment of the present disclosure.

Referring to FIG. 1, an AI system-based vehicle air conditioning control environment may include an AI server 20, a robot 30a, a self-driving vehicle 30b, an XR device 30c, a user terminal 30d, or a home appliance 30e, and a cloud network 10. In this case, in the AI system-based vehicle air conditioning control environment, at least one among the AI server 20, the robot 30a, the self-driving vehicle 30b, the XR device 30c, the user terminal 30d, and the home appliance 30e is connected to the cloud network 10. Here, the robot 30a, the self-driving vehicle 30b, the XR device 30c, the user terminal 30d, or the home appliance 30e, to which AI technology is applied, may be referred to as AI devices 30a to 30e.

The robot 30a may refer to a machine which automatically handles a given task by its own ability, or which operates autonomously. In particular, a robot having a function of recognizing an environment and performing an operation according to its own determination may be referred to as an intelligent robot. Robots 30a may be classified into industrial, medical, household, and military robots, according to the purpose or field of use.

The self-driving vehicle 30b refers to a vehicle which travels without the user's manipulation or with minimal manipulation of the user, and may also be referred to as an autonomous-driving vehicle. For example, autonomous driving may include all of a technology for keeping a driving lane, a technology for automatically controlling a speed such as an adaptive cruise control, a technology for automatically driving a vehicle along a determined path, and a technology for, if a destination is set, automatically setting a path and driving a vehicle along the path. In this case, a self-driving vehicle may be considered as a robot with an autonomous driving function.

The XR device 30c refers to a device using extended reality (XR), which collectively refers to virtual reality (VR), augmented reality (AR), and mixed reality (MR). VR technology provides objects or backgrounds of the real world only in the form of CG images, AR technology provides virtual CG images overlaid on the physical object images, and MR technology employs computer graphics technology to mix and merge virtual objects with the real world. XR technology may be applied to a head-mounted display (HMD), a head-up display (HUD), a mobile phone, a tablet PC, a laptop computer, a desktop computer, a TV, digital signage, and the like. A device employing XR technology may be referred to as an XR device.

The user terminal 30d may be supplied with a service for operating or controlling the vehicle air conditioning control apparatus through an authentication process after accessing a vehicle air conditioning control application or a vehicle air conditioning control site. In the present embodiment, the user terminal 30d which completes the authentication process controls the vehicle air conditioning control system 1 and an operation of the vehicle air conditioning control apparatus 100. In the present embodiment, the user terminal 30d may be a desktop computer, a smartphone, a notebook, a tablet PC, a smart TV, a cell phone, a personal digital assistant (PDA), a laptop, a media player, a micro server, a global positioning system (GPS) device, an electronic book terminal, a digital broadcast terminal, a navigation device, a kiosk, an MP3 player, a digital camera, a home appliance, and other mobile or immobile computing devices operated by the user, but is not limited thereto. In addition, the user terminal 30d may be a wearable terminal having a communication function and a data processing function, such as a watch, glasses, a hair band, and a ring. The user terminal 30d is not limited thereto. Any terminal that is capable of performing web browsing may be used without limitation.

The home appliance 30e may include any one of all electronic devices provided in a home. In particular, the home appliance 30e may include a terminal capable of implementing voice recognition, artificial intelligence, and the like, and a terminal for outputting at least one of an audio signal and a video signal. In addition, the home appliance 30e may include various home appliances (for example, a washing machine, a drying machine, a clothes processing apparatus, an air conditioner, a kimchi refrigerator, or the like) without being limited to specific electronic devices.

The cloud network 10 may include part of the cloud computing infrastructure or refer to a network existing in the cloud computing infrastructure. Here, the cloud network 10 may be constructed by using the 3G network, 4G or Long Term Evolution (LTE) network, or a 5G network. That is, the respective devices (30a to 30e, 20) constituting the AI system-based vehicle air conditioning control environment may be connected to each other through the cloud network 10. In particular, each individual device (30a to 30e, 20) may communicate with each other through the base station but may communicate directly to each other without relying on the base station.

The cloud network 10 may include, for example, wired networks such as local area networks (LANs), wide area networks (WANs), metropolitan area networks (MANs), and integrated service digital networks (ISDNs), or wireless networks such as wireless LANs, CDMA, Bluetooth, and satellite communication, but the scope of the present disclosure is not limited thereto. Furthermore, the cloud network 10 may transmit and receive information using short-range communications or long-distance communications. The short-range communication may include Bluetooth®, radio frequency identification (RFID), infrared data association (IrDA), ultra-wideband (UWB), ZigBee®, and Wi-Fi (wireless fidelity) technologies, and the long-range communication may include code division multiple access (CDMA), frequency division multiple access (FDMA), time division multiple access (TDMA), orthogonal frequency division multiple access (OFDMA), and single carrier frequency division multiple access (SC-FDMA).

The cloud network 10 may include connection of network elements such as hubs, bridges, routers, switches, and gateways. The cloud network 10 may include one or more connected networks, including a public network such as the Internet and a private network such as a secure corporate private network. For example, the network may include a multi-network environment. The access to the cloud network 10 may be provided via one or more wired or wireless access networks. Furthermore, the cloud network 10 may support 5G communication and/or an Internet of things (IoT) network for exchanging and processing information between distributed components such as objects.

The AI server 20 may include a server performing AI processing and a server performing computations on big data. In addition, the AI server 20 may be a database server that provides big data necessary for applying various AI algorithms and data for operating the vehicle air conditioning control system 1. In addition, the AI server 20 may include a web server or an application server which remotely controls an operation of the vehicle air conditioning control apparatus 100 using a vehicle air conditioning control application loaded in the user terminal 30d or a vehicle air conditioning control web browser.

The AI server 20 may be connected to at least one among the AI devices constituting the AI system-based vehicle air conditioning control environment, that is, the robot 30a, the self-driving vehicle 30b, the XR device 30c, the user terminal 30d, and the home appliance 30e, through the cloud network 10, and may assist at least part of AI processing of the connected AI devices 30a to 30e. At this time, the AI server 20 may train the AI network according to the machine learning algorithm instead of the AI devices 30a to 30e, and may directly store the learning model or transmit the learning model to the AI devices 30a to 30e. At this time, the AI server 20 may receive input data from the AI device 30a to 30e, infer a result value from the received input data by using the learning model, generate a response or control instruction based on the inferred result value, and transmit the generated response or control instruction to the AI device 30a to 30e. Similarly, the AI device 30a to 30e may infer a result value from the input data by employing the learning model directly and generate a response or control instruction based on the inferred result value.

Artificial intelligence (AI) is an area of computer engineering science and information technology that studies methods to make computers mimic intelligent human behaviors such as reasoning, learning, self-improving, and the like.

In addition, artificial intelligence (AI) does not exist on its own, but is rather directly or indirectly related to a number of other fields in computer science. In recent years, there have been numerous attempts to introduce an element of AI into various fields of information technology to solve problems in the respective fields.

Machine learning is an area of artificial intelligence that includes the field of study that gives computers the capability to learn without being explicitly programmed. Specifically, the Machine Learning can be a technology for researching and constructing a system for learning, predicting, and improving its own performance based on empirical data and an algorithm for the same. Machine learning algorithms, rather than only executing rigidly set static program instructions, may take an approach that builds models for deriving predictions and decisions from inputted data.

The present embodiment particularly relates to the self-driving vehicle 30b. Thus, among the above-mentioned AI devices to which the technology is applied, the self-driving vehicle 30b will be described in the embodiments below. However, in the present embodiment, the vehicle (200 of FIG. 2) is not limited to the self-driving vehicle 30b, and may refer to any vehicles, including the self-driving vehicle 30b and general vehicles. In the present embodiment, a vehicle in which the vehicle air conditioning control system 1 is disposed may be an embodiment.

Figure 2:
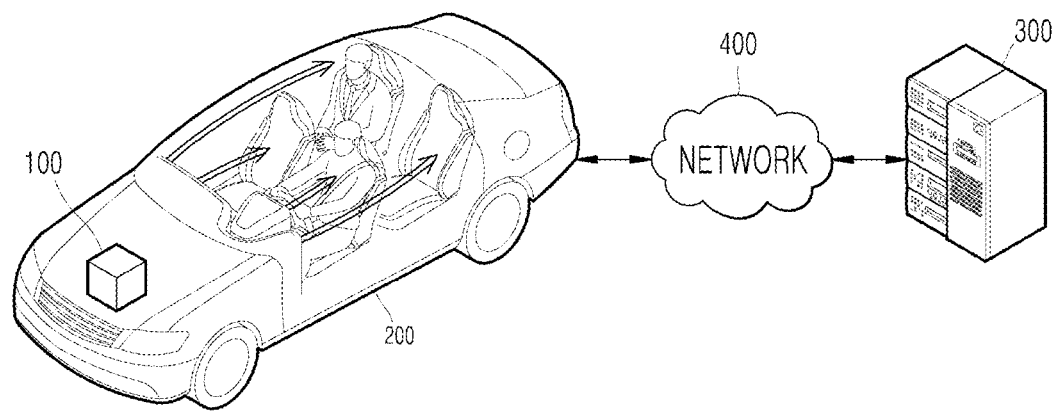
FIG. 2 is a view for schematically explaining a vehicle air conditioning control communication environment according to an embodiment of the present disclosure.

FIG. 2 is a diagram schematically illustrating a communication environment of a vehicle air conditioning control according to an embodiment of the present disclosure. In the following description, description of parts overlapping with those of FIG. 1 will be omitted.

Referring to FIG. 2, the vehicle air conditioning control system includes the vehicle air conditioning control apparatus 100, the vehicle 200, the server 300, and the network 400 as essential components and further includes a component such as a user terminal as an additional component. Further, even though not specifically illustrated in the drawing, the vehicle 200 includes an air conditioner and the air conditioner is controlled by the vehicle air conditioning control apparatus 100. In this case, the vehicle air conditioning control apparatus 100 may be disposed in the vehicle 200, but is not limited thereto. Further, in the present embodiment, a user may refer to a driver of the vehicle 200 and other passengers may refer to passengers other than the driver. Further, a driver of the vehicle 200 may be a driver which is registered in advance in the vehicle 200 and one or more drivers may be registered in advance. In a call in the vehicle 200 using a hands-free function, a near-end speaker refers to a user who talks on the phone in the vehicle 200 and a far-end speaker refers to a counterpart user who talks on the phone with the near-end speaker. Further, a user which talks on the phone in the vehicle 200 may be a driver, but is not limited thereto, and may refer to other passengers in the vehicle 200 who talk on the phone using a hands-free function in the vehicle 200.

In the present embodiment, the air conditioner may include a driving module including a motor configured to adjust a direction of the wind and a motor configured to adjust wind volume and an air conditioning discharging port.

The air conditioning system is a concept including one or more air conditioners, a plurality of controllers which controls the air conditioners, wireless controllers corresponding thereto, and a central controller which controls the entire air conditioners. The air conditioning system may be described as a concept including the air conditioning control apparatus 100 which controls the air conditioner in the vehicle according to the embodiment of the present disclosure. The air conditioning system may refer to a system which implements air conditioning such as cooling or heating in a target space included in structures such as houses, buildings, factories, and public facilities, as well as the vehicle.

The vehicle air conditioning control apparatus 100 which controls the air conditioner in the vehicle 200 may transmit various data to the server 300 and receive various data from the server 300. For example, the server 300 receives data to be used as learning data from the vehicle air conditioning control apparatus 100 and the vehicle air conditioning control apparatus 100 may transmit user log data as learning data to the server 300.

Further, the vehicle air conditioning control apparatus 100 may communicate with the server 300 to perform processes of generating, maintaining, and updating various programs related to an artificial intelligence model which estimates thermal comfort according to the embodiment of the present disclosure. With regard to this, the server 300 may provide a part or all of the program to the vehicle air conditioning control apparatus 100 through the communication connection. Further, in a state in which communication between the vehicle air conditioning control apparatus 100 and the server 300 according to the embodiment of the present disclosure is not connected, the vehicle air conditioning control apparatus 100 may estimate the thermal comfort of the user using the artificial intelligence model stored in the memory in a local area where the vehicle air conditioning control apparatus 100 belongs, as in online.

In the present embodiment, the vehicle 200 may include a vehicle communication module, a vehicle controller, a vehicle user interface, a driving manipulation module, a vehicle driving module, an operation module, a navigation module, a sensing module, and the like. Depending on the embodiment, the vehicle 200 may include components other than the above-described components, or may not include some of components to be described below.

Here, the vehicle 200 may be a self-driving vehicle, and may be switched from an autonomous driving mode to a manual mode, or switched from the manual mode to the autonomous driving mode according to a user input received through the vehicle user interface. In addition, the vehicle 200 may be switched from an autonomous mode to a manual mode, or switched from the manual mode to the autonomous mode depending on the driving situation. Here, the driving situation may be judged by at least one of the information received by the vehicle communication module, the external object information detected by the sensing module, or the navigation information acquired by the navigation module.

Meanwhile, in the present embodiment, the vehicle 200 may receive a service request (user input) from the user for control. The method by which the vehicle 200 receives the service provision request from the user may include the case of receiving a touch (or button input) signal for the vehicle user interface from the user, the case of receiving the speech corresponding to the service request from the user, and the like. In this case, the touch signal reception, the speech reception, and the like from the user may be possible by the user terminal (30d of FIG. 1). In addition, the speech reception may be provided by a separate microphone which executes a speech recognition function.

When the vehicle 200 is operated in the autonomous mode, the vehicle 200 may be operated according to the control of the travel module that controls traveling, parking, and unparking operations (e.g., getting out of a parking spot). Meanwhile, when the vehicle 200 is driven in the manual mode, the vehicle 200 may be driven by a user input through the driving controller. The vehicle 200 may be connected to an external server through a communication network, and may be capable of moving along a predetermined route without a driver's intervention by using an autonomous driving technique.

The vehicle user interface is provided for communication between the vehicle 200 and the vehicle user and receives an input signal of the user and transmits the received input signal to the vehicle controller and provides information possessed by the vehicle 200 to the user by the control of the vehicle controller. The vehicle user interface may include, but is not limited to, an input interface, an internal camera, a bio-sensing module, and an output interface.

The input interface is for receiving information from a user. The data collected by the input interface may be analyzed by the vehicle controller and processed by the user's control instruction. The input interface may receive the destination of the vehicle 200 from the user and provide the destination to the controller. The input interface may input to the vehicle controller a signal for designating and deactivating at least one of the plurality of sensor modules of the sensor according to the user's input. The input interface may be disposed inside the vehicle. For example, the input interface may be disposed on one area of a steering wheel, one area of an instrument panel, one area of a seat, one area of each pillar, one area of a door, one area of a center console, one area of a head lining, one area of a sun visor, one area of a windshield, or one area of a window. Specifically, in the present embodiment, the input interface may include one or more microphones (2 of FIG. 3) which collect a sound signal in the vehicle.

The output interface generates a visual, auditory, or tactile related output and outputs a sound or an image. Furthermore, the output interface may include at least one of a display, a sound output interface, and a haptic output interface.

The display may display graphic objects corresponding to various information. The display may include at least one of a liquid crystal display (LCD), a thin film transistor liquid crystal display (TFT LCD), an organic light emitting diode (OLED), a flexible display, a 3D display, or an e-ink display. The display may have a mutual layer structure with a touch input interface, or may be integrally formed to implement a touch screen. The display may be implemented as a head up display (HUD). When the display is implemented as an HUD, the display may include a projection module to output information through an image projected onto a windshield or a window. The display may include a transparent display. The transparent display may be attached to the windshield or the window. The transparent display may display a predetermined screen with a predetermined transparency. The transparent display may include at least one of a transparent thin film electroluminescent (TFEL), a transparent organic light-emitting diode (OLED), a transparent liquid crystal display (LCD), a transmissive transparent display, or a transparent light emitting diode (LED). The transparency of the transparent display may be adjusted. The vehicle user interface may include a plurality of displays. The display may be disposed in one area of the steering wheel, one area of the instrument panel, one area of the seat, one area of each pillar, one area of the door, one area of the center console, one area of the head lining, or one area of the sun visor, or may be implemented on one area of the windshield or one area of the window.

The sound output interface may convert an electrical signal provided from the vehicle controller into an audio signal. To this end, the sound output interface may include one or more speakers (3 of FIG. 3). The haptic output interface may generate a tactile output. For example, the haptic output interface may operate to allow the user to perceive the output by vibrating a steering wheel, a seat belt, and a seat.

The driving manipulation module may receive a user input for driving. In the case of the manual mode, the vehicle 200 may operate based on the signal provided by the driving controller. That is, the driving manipulation module may receive an input for the operation of the vehicle 200 in the manual mode, and may include a steering input interface, an acceleration input interface, and a brake input interface, but the present disclosure is not limited thereto.

The vehicle driving module may electrically control the driving of various devices in the vehicle 200, and may include a powertrain driving module, a chassis driving module, a door/window driving module, a safety device driving module, a lamp driving module, and an air conditioning driving module, but the present disclosure is not limited thereto.

The operation module may control various operations of the vehicle 200, and in particular, may control various operations of the vehicle 200 in the autonomous driving mode. The operation module may include a driving module, an unparking module, and a parking module, but the present disclosure is not limited thereto. Further, the operation module may include a processor which is controlled by the vehicle controller. Each module of the operation module may include a processor individually. According to the embodiment, when the operation module is implemented as software, the operation module may be a sub concept of the vehicle controller.

In this case, the driving module, the unparking module, and the parking module may drive, unpark, and park the vehicle 200, respectively. Further, the driving module, the unparking module, and the parking module are provided with object information from the sensing module to provide a control signal to the vehicle driving module to drive, unpark, and park the vehicle 200. Further, the driving module, the unparking module, and the parking module are provided with a signal from an external device through the vehicle communication module to provide the control signal to the vehicle driving module to drive, unpark, and park the vehicle 200. Further, the driving module, the unparking module, and the parking module are provided with navigation information from the navigation module to provide a control signal to the vehicle driving module to drive, unpark, and park the vehicle 200. The navigation module may provide the navigation information to the vehicle controller. The navigation information may include at least one of map information, set destination information, route information according to destination setting, information about various objects on the route, lane information, or current location information of the vehicle. The navigation module may provide the vehicle controller with a parking lot map of the parking lot entered by the vehicle 200. When the vehicle 200 enters the parking lot, the vehicle controller receives the parking lot map from the navigation module, and projects the calculated route and fixed identification information on the provided parking lot map so as to generate the map data. The navigation module may include a memory. The memory may store navigation information. The navigation information may be updated by information received through the vehicle communication module. The navigation module may be controlled by an internal processor, or may operate by receiving an external signal, for example, a control signal from the vehicle controller, but the present disclosure is not limited thereto.

The sensing module may sense the state of the vehicle 200 using a sensor mounted on the vehicle 200, that is, a signal related to the state of the vehicle 200, and obtain movement route information of the vehicle 200 according to the sensed signal. Further, the sensing module may provide the acquired movement route information to the vehicle controller. The sensing module may sense objects near the vehicle 200 by using a sensor mounted on the vehicle 200.

The sensing module is for detecting an object located outside the vehicle 200. The sensing module may generate object information based on the sensing data, and transmit the generated object information to the vehicle controller. Examples of the object may include various objects related to the driving of the vehicle 200, such as a lane, another vehicle, a pedestrian, a motorcycle, a traffic signal, light, a road, a structure, a speed bump, a landmark, and an animal. The sensing module is a plurality of sensor modules and includes a camera module, a lidar (light imaging detection and ranging), an ultrasonic sensor, a radar (radio detection and ranging), and an infrared sensor. The sensing module may sense environment information around the vehicle 200 by means of the plurality of sensor modules. Depending on the embodiment, the sensing module may further include other components in addition to the above-mentioned components, or may not include some of the above-mentioned components. The radar may include an electromagnetic wave transmitting module and an electromagnetic wave receiving module. The radar may be implemented using a pulse radar method or a continuous wave radar method in terms of radio wave emission principle. The radar may be implemented using a frequency modulated continuous wave (FMCW) method or a frequency shift keying (FSK) method according to a signal waveform in a continuous wave radar method. The radar may detect an object based on a time-of-flight (TOF) method or a phase-shift method using an electromagnetic wave as a medium, and detect the location of the detected object, the distance to the detected object, and the relative speed of the detected object. The radar may be disposed at an appropriate location outside the vehicle 200 for sensing objects located at the front, back, or side of the vehicle 200.

The lidar may include a laser transmitter, and a laser receiver. The lidar may be embodied using the time of flight (TOF) method or in the phase-shift method. The lidar may be implemented as a driven type or a non-driven type. When the lidar is embodied in the driving method, the lidar may rotate by means of a motor, and detect an object near the vehicle 200. When the lidar is implemented in the non-driving method, the lidar may detect an object within a predetermined range with respect to the vehicle 200 by means of light steering. The vehicle 200 may include a plurality of non-driven type lidars. The lidar may detect an object using the time of flight (TOF) method or the phase-shift method using laser light as a medium, and detect the location of the detected object, the distance from the detected object and the relative speed of the detected object. The lidar may be disposed at an appropriate location outside the vehicle 200 for sensing objects located at the front, back, or side of the vehicle 200.

The image capturer may be disposed at a suitable place outside the vehicle 200, for example, the front, back, right side mirrors and the left side mirror of the vehicle 200, in order to acquire a vehicle exterior image. The image capturer may be a mono camera, but is not limited thereto. The image capturer may be a stereo camera, an around view monitoring (AVM) camera, or a 360-degree camera. The image capturer may be disposed close to the front windshield in the interior of the vehicle 200 in order to acquire an image of the front of the vehicle 200. The image capturer may be disposed around the front bumper or the radiator grill. The image capturer may be disposed close to the rear glass in the interior of the vehicle 200 in order to acquire an image of the back of the vehicle 200. The image capturer may be disposed around the rear bumper, the trunk, or the tail gate. The image capturer may be disposed close to at least one of the side windows in the interior of the vehicle 200 in order to acquire an image of the side of the vehicle 200. In addition, the image capturer may be disposed around the fender or the door.

The ultrasonic sensor may include an ultrasonic transmitter, and an ultrasonic receiver. The ultrasonic sensor may detect an object based on ultrasonic waves, and detect the location of the detected object, the distance from the detected object, and the relative speed of the detected object. The ultrasonic sensor may be disposed at an appropriate location outside the vehicle 200 for sensing objects located at the front, back, or side of the vehicle 200. The infrared sensor may include an infrared transmitter and an infrared receiver. The infrared sensor may detect an object based on infrared light, and detect the position of the detected object, the distance from the detected object, and the relative speed of the detected object. The infrared sensor may be disposed at an appropriate location outside the vehicle 200 for sensing objects located at the front, back, or side of the vehicle 200.

The vehicle controller may control the overall operation of each module of the sensing module. The vehicle controller may compare data sensed by the radar, the lidar, the ultrasonic sensor, and the infrared sensor with pre-stored data so as to detect or classify an object. The vehicle controller may detect and track the object based on the acquired image. The vehicle controller may perform operations such as calculation of the distance from an object and calculation of the relative speed of the object through image processing algorithms. For example, the vehicle controller may obtain the distance information from the object and the relative speed information of the object from the acquired image based on the change of size of the object over time. For example, the vehicle controller may obtain the distance information from the object and the relative speed information of the object through, for example, a pin hole model and road surface profiling.

The vehicle controller may detect and track the object based on a reflected wave (or reflected light) of at least one of the transmitted electromagnetic wave, laser, ultrasonic wave, and infrared ray which is reflected from the object to return. In this case, the vehicle controller may perform an operation to calculate a distance from the object and calculate a relative speed with respect to the object, based on the reflected wave (reflected light). Depending on the embodiment, the sensing module may include a processor separate from the vehicle controller. In addition, the radar, the lidar, the ultrasonic sensor, and the infrared sensor may each include a processor. When the processor is included in the sensing module, the sensing module may operation in accordance with the control of the processor which is controlled by the vehicle controller.

The sensing module may include a posture sensor (for example, a yaw sensor, a roll sensor, and a pitch sensor), a collision sensor, a wheel sensor, a speed sensor, a tilt sensor, a weight sensor, a heading sensor, a gyro sensor, a position module, a vehicle forward/reverse movement sensor, a battery sensor, a fuel sensor, a tire sensor, a steering sensor by rotation of a steering wheel, a vehicle interior temperature sensor, a vehicle interior humidity sensor, an ultrasonic sensor, an illuminance sensor, an accelerator pedal position sensor, and a brake pedal position sensor. The sensing module may further include an acceleration pedal sensor, a pressure sensor, an engine speed sensor, an air flow sensor (AFS), an air temperature sensor (ATS), a water temperature sensor (WTS), a throttle position sensor (TPS), a TDC sensor, a crank angle sensor (CAS). The sensing module may generate vehicle state information based on sensing data. The vehicle state information may be information generated based on data sensed by various sensors included in the inside of the vehicle. Vehicle state information may include, for example, attitude information of the vehicle, speed information of the vehicle, tilt information of the vehicle, weight information of the vehicle, direction information of the vehicle, battery information of the vehicle, fuel information of the vehicle, tire air pressure information of the vehicle, steering information of the vehicle, interior temperature information of the vehicle, interior humidity information of the vehicle, pedal position information, or vehicle engine temperature information.

The server 300 may provide a program required to generate and train an artificial intelligence model which estimates thermal comfort according to an embodiment of the present disclosure to the vehicle air conditioning control apparatus 100. Alternatively, the server 300 may directly generate and train the artificial intelligence model and then provide the completed artificial intelligence model to the vehicle air conditioning control apparatus 100. The server 300 may collect data to be used to train the artificial intelligence model in the form of user log data that uses the vehicle air conditioning control apparatus 100, that is, the air conditioner. The server 300 may be configured by a plurality of computing devices which performs one or all the functions related to the functions related to generating and training the artificial intelligence model for estimating the thermal comfort according to the embodiment of the present disclosure and the collecting of learning data.

Further, in the present embodiment, the server 300 may include the AI server 20 of FIG. 1, a mobile edge computing (MEC) server, and a server for a process of the vehicle air conditioning control apparatus 100, or may be a general name thereof. When the server 300 is another server that is not specified in the present embodiment, the connection relationship illustrated in FIG. 2 may be changed.

The AI server receives data for air conditioning control from the vehicle 200 to analyze thermal comfort information of the user and other passengers collected in the vehicle and perform the learning to control the air conditioning in the vehicle in response to the result acquired by analyzing the thermal comfort information. The AI server transmits a result acquired by analyzing the thermal comfort information of the user and other passengers and a learning result for controlling the air conditioning in the vehicle in response to the result to the vehicle 200 to allow the vehicle 200 to perform an operation for controlling the air conditioning, that is, control the air conditioning such as wind direction and the wind volume in response to the thermal comfort information of the user and other passengers.

The MEC server may act as a general server, and may be connected to a base station (BS) next to a road in a radio access network (RAN) to provide flexible vehicle-related services and efficiently operate the network 400. In particular, network-slicing and traffic scheduling policies supported by the MEC server can assist the optimization of the network 400. The MEC server is integrated inside the RAN, and may be located in an S1-user plane interface (for example, between the core network and the base station) in the 3GPP system. The MEC server may be regarded as an independent network element, and does not affect the connection of the existing wireless networks. The independent MEC servers may be connected to the base station via the dedicated communication network and may provide specific services to various end-users located in the cell. These MEC servers and the cloud servers may be connected to each other through an Internet-backbone, and share information with each other. The MEC server may operate independently, and control a plurality of base stations. Specifically, the MEC servers may perform a service for a self-driving vehicle, an application operation such as a virtual machine (VM), and an operation at a mobile network edge stage based on a virtualization platform. The base station (BS) is connected to all the MEC servers and a core network to enable flexible user traffic scheduling required to perform the provided service. When a large amount of user traffic occurs in a specific cell, the MEC server may perform task offloading and collaborative processing based on the interface between neighboring base stations. That is, since the MEC server has an open operating environment based on software, new services of an application provider may be easily provided. Since the MEC server performs the service at a location near the end-user, the data round-trip time is shortened and the service providing speed is high, thereby reducing the service waiting time. MEC applications and virtual network functions (VNFs) may provide flexibility and geographic distribution in service environments. When using this virtualization technology, various applications and network functions can be programmed, and only specific user groups may be selected or compiled for them. Therefore, the provided services may be applied more closely to user requirements. In addition to centralized control ability, the MEC server may minimize interaction between base stations. This may simplify the process for performing basic functions of the network, such as handover between cells. This function may be particularly useful in autonomous driving systems used by a large number of users. In the autonomous driving system, the terminals of the road may periodically generate a large amount of small packets. In the RAN, the MEC server may reduce the amount of traffic that must be delivered to the core network by performing certain services. This may reduce the processing burden of the cloud in a centralized cloud system, may minimize network congestion. The MEC server integrates a network control function and individual services, which increases the profitability of mobile network operators (MNOs) thereby and promptly and effectively perform the maintenance and the upgrade by adjusting an installation density. In the meantime, the network 400 may refer to the cloud network 10 of FIG. 1 so that a detailed description thereof will be omitted.

Figure 3:
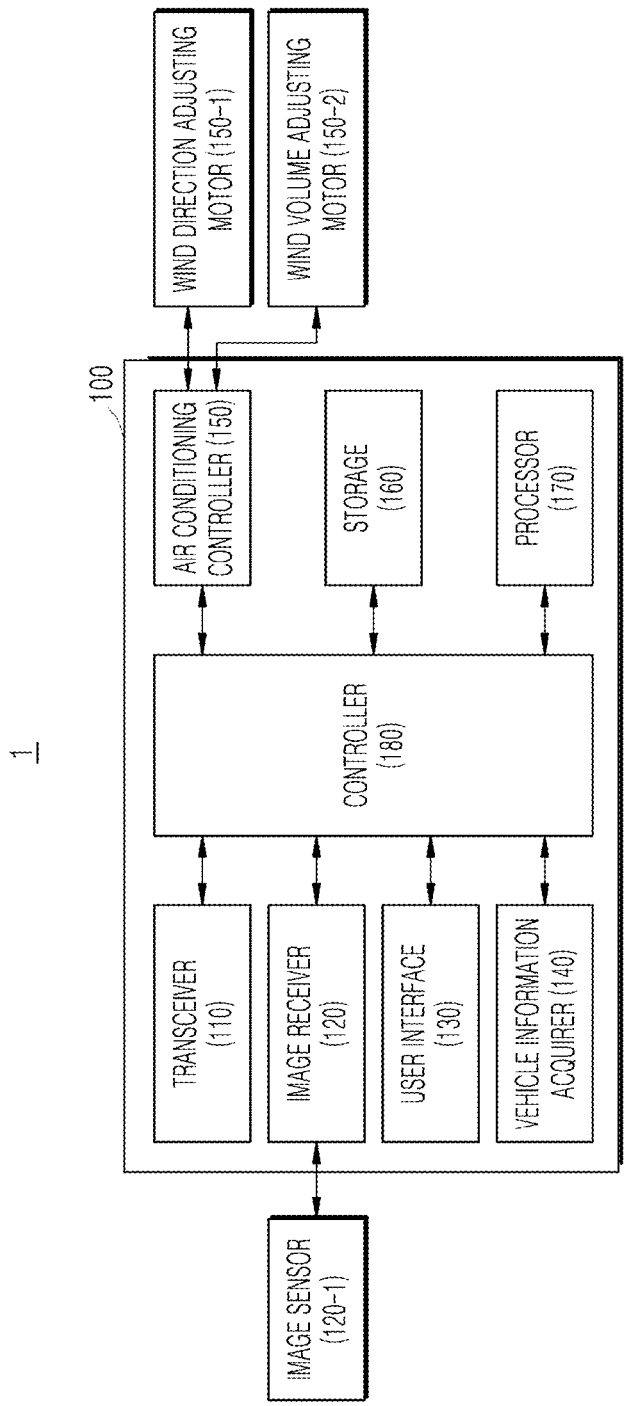
FIG. 3 is a schematic block diagram of a vehicle air conditioning control system according to an embodiment of the present disclosure.

FIG. 3 is a schematic block diagram of a vehicle air conditioning control system according to an embodiment of the present disclosure. In the following description, description of parts that are the same as those in FIG. 1 and FIG. 2 will be omitted.

Referring to FIG. 3, the vehicle air conditioning control system 1 may include an image sensor 120-1, a vehicle air conditioning control apparatus 100, a wind direction adjusting motor 150-1, and a wind volume adjusting motor 150-2. In the present embodiment, in order to control the air conditioner in the vehicle, the vehicle air conditioning control apparatus 100 may perform a function of estimating thermal comfort and controlling the air conditioning based on the estimated thermal comfort information, among various control functions, based on the thermal image collected through the image sensor 120-1. That is, the vehicle air conditioning control apparatus 100 may acquire a thermal image in the vehicle using the image sensor 120-1. The vehicle air conditioning control apparatus 100 may acquire thermal comfort information of each passenger in the vehicle using the acquired thermal image. Further, the vehicle air conditioning control apparatus 100 may drive the wind direction adjusting motor 150-1 and the wind volume adjusting motor 150-2 based on the thermal comfort information of each passenger to control the air conditioning of the vehicle.

The image sensor 120-1 acquires images of a user and other passengers in the vehicle. In the present embodiment, the image sensor 120-1 may be a camera which is a basis of the thermal comfort estimation, that is, a thermal infrared camera.

The thermal infrared camera may consistently generate a visual thermal image which is displayed on a screen with the assistance of a thermal sensor and a circuitry. The thermal infrared camera may output a thermal image in which a temperature is displayed in accordance with a thermal distribution of a subject. A lens of the thermal infrared camera may be focused on an object or a specific area. The lens of the camera is focused on an infrared heat emitted from all objects in a field of view of the camera lens and scans the light with an infrared sensor in the camera. A thermal detector in the thermal infrared camera may generate a detailed temperature pattern, which is called as a thermal image, in one second. The temperature information may be collected from thousands of points in the field of view of the thermal detector. The thermal image generated by an element of the camera may be converted into an electric signal (impulse). The electric signal may be sent to a special circuit board having a chip which converts information of visible data of a detector element from a display of the camera or a separate display. The signal creates a thermal image having various colors in accordance with an intensity of emitted infrared ray. The higher the temperature, the brighter the color. In the present embodiment, light scanning, condensing, detecting, amplifying, displaying, and synchronization of scanning and displaying are performed in the thermal image generating step. The thermal infrared camera may be equipped at the side of a room mirror to easily photograph all the user and other passengers in the vehicle, but is not limited thereto and may be provided in one or more locations.

In the present embodiment, the thermal comfort-based vehicle air conditioning control apparatus 100 may include a unit for controlling the air conditioning which satisfies the thermal comfort based on personal thermal comfort information. That is, the vehicle air conditioning control apparatus 100 may include a device required to control a discharging angle and a discharging amount of air flow to control a strength and a direction of the air flow differently for the user and other passengers in the vehicle. That is, in the present embodiment, the wind direction adjusting motor 150-1 and the wind volume adjusting motor 150-2 may be included. The wind direction adjusting motor 150-1 may adjust the discharging angle of an air conditioning discharging port to vary the discharging direction of the discharged air. Further, the wind volume adjusting motor 150-2 may vary the discharged amount of the air discharged through the air conditioning discharging port. In this case, the implementing method and the driving method of the wind direction adjusting motor 150-1 and the wind volume adjusting motor 150-2 are not specifically limited, but specifically, the wind direction adjusting motor 150-1 may be implemented by a servomotor.

To be more specific, the vehicle air conditioning control apparatus 100 may include a transceiver 110, an image receiver 120, a user interface 130, a vehicle information receiver 140, an air conditioning controller 150, a storage 160, a processor 170, and a controller 180.

The transceiver 110 may be a vehicle communication module which performs communication between the vehicle 200 and an external device. The transceiver 110 may support communication in a plurality of communication modes, receive a server signal from the server, and transmit a signal to the server. In addition, the transceiver 110 may receive a signal from another vehicle, transmit a signal to another vehicle, receive a signal from the user terminal, and transmit a signal to the user terminal. That is, the external device may include another vehicle, a user terminal, and a server system. Further, the transceiver 110 may include a communication module for communication in the vehicle. Here, the plurality of communication modes may include an inter-vehicle communication mode which performs the communication with the other vehicle, a server communication mode which performs communication with an external server, a short distance communication mode which performs communication with a user terminal such as a user terminal in the vehicle, and an in-vehicle communication mode which communicates with units in the vehicle. That is, the transceiver 110 may include a wireless transceiver, a V2X transceiver, a short-range transceiver, and the like. The transceiver 110 may further include a location information module which receives a signal including location information of the vehicle 200. The location information module may include a Global Positioning System (GPS) module or a Differential Global Positioning System (DGPS) module.

The wireless transceiver may transmit and receive signals to and from a user terminal or a server through a mobile communication network. Here, the mobile communication network is a multiple access system capable of supporting communication with multiple users by sharing used system resources (bandwidth, transmission power, or the like). Examples of the multiple access system include a code division multiple access (CDMA) system, a frequency division multiple access (FDMA) system, a time division multiple access (TDMA) system, an orthogonal frequency division multiple access (OFDMA) system, a single carrier frequency division multiple access (SC-FDMA) system, and a multi-carrier frequency division multiple access (MC-FDMA) system.

The V2X transceiver may transmit and receive a signal with an RSU through a V2I communication protocol in a wireless manner, may transmit and receive a signal with another vehicle, that is, a vehicle near the vehicle 200 within a certain distance, through a V2V communication protocol, and may transmit and receive a signal to and from a user terminal, that is, a pedestrian or a user, through a V2P communication protocol. The V2X transceiver may include an RF circuit capable of implementing V2I, V2V, and V2P communication protocols. That is, the transceiver 110 may include at least one among a transmit antenna and a receive antenna for performing communication, and a radio frequency (RF) circuit and an RF element capable of implementing various communication protocols.

The short-range transceiver may be connected to the user terminal of the driver through a short-range wireless communication module. In this case, the short-range transceiver may be connected to the user terminal through wired communication as well as wireless communication. For example, if the driver's user terminal is registered in advance, the short-range transceiver may automatically connect with the vehicle 200 when the registered user terminal is recognized within a predetermined distance from the vehicle 200 (for example, in the vehicle). That is, the transceiver 110 may perform short-range communication, GPS signal reception, V2X communication, optical communication, broadcast transmission and reception, and intelligent transport systems (ITS) communication. The transceiver 110 may support short-range communication by using at least one of Bluetooth, Radio Frequency Identification (RFID), Infrared Data Association (IrDA), Ultra Wideband (UWB), ZigBee, Near Field Communication (NFC), Wireless Fidelity (Wi-Fi), Wi-Fi Direct, or Wireless Universal Serial Bus (Wireless USB) technologies. The transceiver 110 may further support other functions than the functions described, or may not support some of the functions described, depending on the embodiment.

Depending on the embodiment, the overall operation of each module of the transceiver 110 may be controlled by a separate processor provided in the transceiver 110. The transceiver 110 may include a plurality of processors, or may not include a processor. When a processor is not included in the transceiver 110, the transceiver 110 may be operated by either a processor of another apparatus in the vehicle 200 or the vehicle controller. In addition, the transceiver 110 may, together with the vehicle user interface, implement a vehicle-use display. In this case, the vehicle display device may be referred to as a telematics device or an audio video navigation (AVN) device.

In the meantime, in the present embodiment, the transceiver 110 may receive thermal comfort information of each passenger in the vehicle acquired based on one or more of a first deep neural network model and a second deep neural network model which are trained in advance to analyze a skin temperature feature and extracts a thermal comfort of a human body, based on a downlink grant of a 5G network connected to drive the vehicle 200 in which the vehicle air conditioning control system 1 is disposed in an autonomous driving mode.

Figure 4:
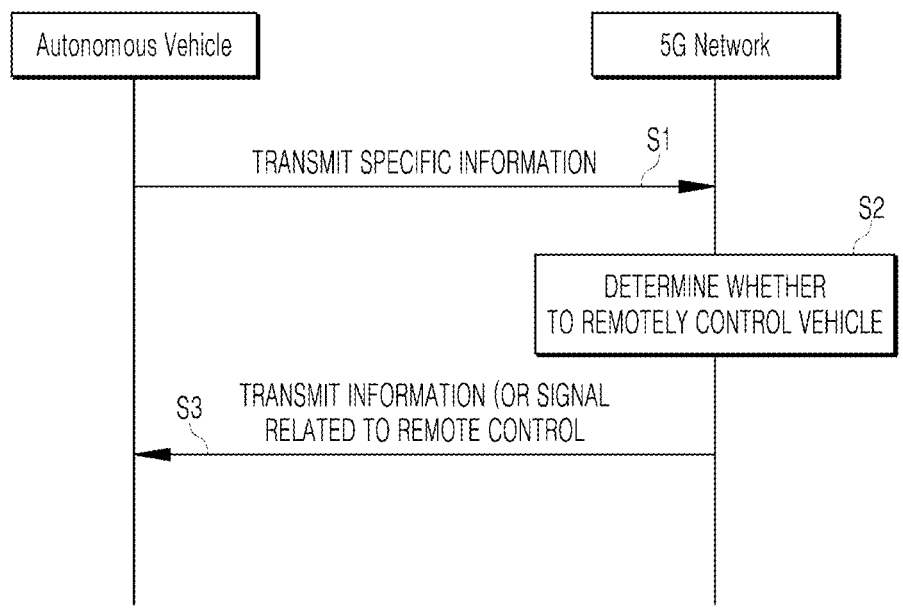
FIG. 4 illustrates an example of basic operations of a self-driving vehicle and a 5G network in a 5G communication system.
Figure 5:
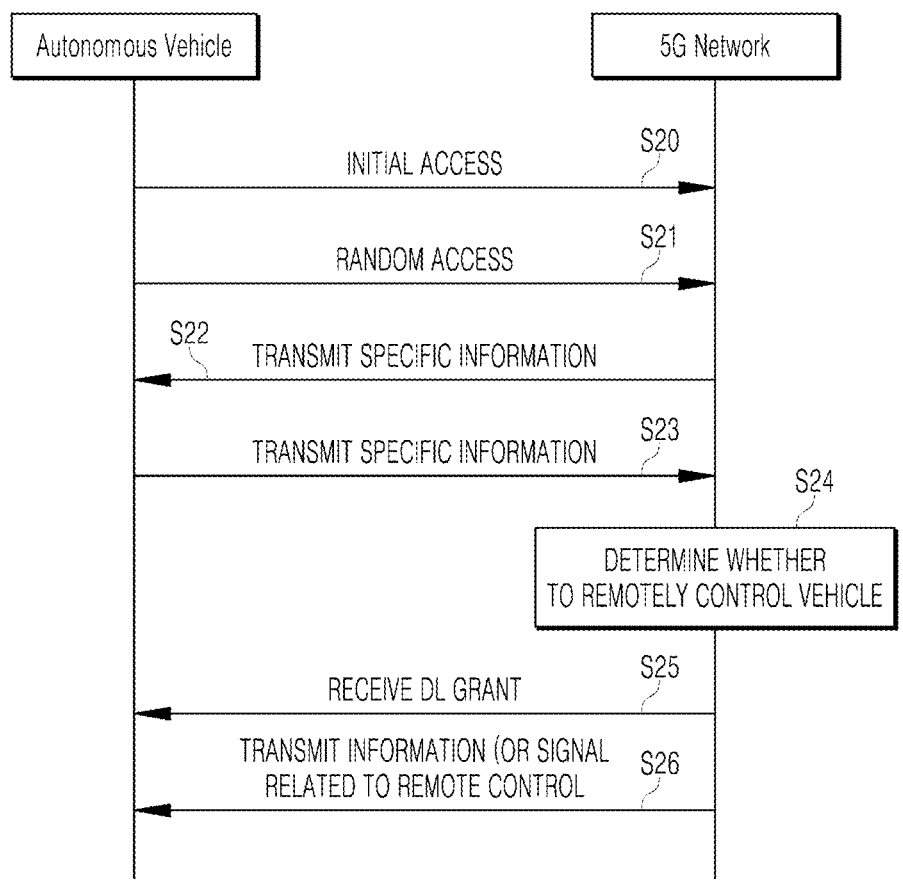
FIG. 5 illustrates an example of application operations of a self-driving vehicle and a 5G network in a 5G communication system.

FIG. 4 is a diagram illustrating an example of the basic operation of a self-driving vehicle and a 5G network in a 5G communication system.

The transceiver 110 may transmit specific information over a 5G network when the vehicle 200 is operated in the autonomous driving mode.

The specific information may include autonomous driving related information.

The autonomous driving related information may be information directly related to the driving control of the vehicle. For example, the autonomous driving related information may include at least one among object data indicating an object near the vehicle, map data, vehicle status data, vehicle location data, and driving plan data.

The autonomous driving related information may further include service information necessary for autonomous driving. For example, the specific information may include information about the destination and the safety rating of the vehicle, which are inputted through the user interface 130 as shown in FIG. 3.

In addition, the 5G network may determine whether the vehicle is remotely controlled (S2).

The 5G network may include a server or a module for performing remote control related to autonomous driving.

The 5G network may transmit information (or a signal) related to the remote control to a self-driving vehicle (S3).

As described above, information related to the remote control may be a signal directly applied to the self-driving vehicle, and may further include service information necessary for autonomous driving. The self-driving vehicle according to this embodiment may receive service information such as insurance for each interval selected on a driving route and risk interval information, through a server connected to the 5G network to provide services related to the autonomous driving.

An essential process for performing 5G communication between the self-driving vehicle 200 and the 5G network (for example, an initial access process between the vehicle and the 5G network) will be briefly described with reference to FIG. 5 to FIG. 9 below.

An example of application operations through the self-driving vehicle 200 performed in the 5G communication system and the 5G network is as follows.

The vehicle 200 may perform an initial access process with the 5G network (initial access step, S20). In this case, the initial access procedure includes a cell search process for acquiring downlink (DL) synchronization and a process for acquiring system information.

The vehicle 200 may perform a random access process with the 5G network (random access step, S21). At this time, the random access procedure includes an uplink (UL) synchronization acquisition process or a preamble transmission process for UL data transmission, a random access response reception process, and the like.

The 5G network may transmit an Uplink (UL) grant for scheduling transmission of specific information to the self-driving vehicle 200 (UL grant receiving step, S22).

The procedure by which the vehicle 1000 receives the UL grant includes a scheduling process in which a time/frequency resource is allocated for transmission of UL data to the 5G network.

The self-driving vehicle 200 may transmit specific information over the 5G network based on the UL grant (specific information transmission step, S23).

The 5G network may determine whether the vehicle 200 is to be remotely controlled based on the specific information transmitted from the vehicle 200 (vehicle remote control determination step, S24).

The self-driving vehicle 200 may receive the DL grant through a physical DL control channel for receiving a response on pre-transmitted specific information from the 5G network (DL grant receiving step, S25).

The 5G network may transmit information (or a signal) related to the remote control to the self-driving vehicle 200 based on the DL grant (remote control related information transmission step, S26).

A process in which the initial access process and/or the random access process between the 5G network and the self-driving vehicle 200 is combined with the DL grant receiving process has been exemplified. However, the present disclosure is not limited thereto.

For example, an initial access procedure and/or a random access procedure may be performed through an initial access step, an UL grant reception step, a specific information transmission step, a remote control determination step of the vehicle, and an information transmission step associated with remote control. Further, an initial access procedure and/or a random access procedure may be performed through a random access step, an UL grant reception step, a specific information transmission step, a remote control determination step of the vehicle, and an information transmission step associated with remote control. The self-driving vehicle 200 may be controlled by the combination of an AI operation and the DL grant receiving process through the specific information transmission step, the vehicle remote control determination step, the DL grant receiving step, and the remote control related information transmission step.

The operation of the self-driving vehicle 200 described above is merely exemplary, but the present disclosure is not limited thereto.

For example, the operation of the self-driving vehicle 200 may be performed by selectively combining the initial access step, the random access step, the UL grant receiving step, or the DL grant receiving step with the specific information transmission step, or the remote control related information transmission step. The operation of the self-driving vehicle 200 may include the random access step, the UL grant receiving step, the specific information transmission step, and the remote control related information transmission step. The operation of the self-driving vehicle 200 may include the initial access step, the random access step, the specific information transmission step, and the remote control related information transmission step. The operation of the self-driving vehicle 200 may include the UL grant receiving step, the specific information transmission step, the DL grant receiving step, and the remote control related information transmission step.

Figure 6:
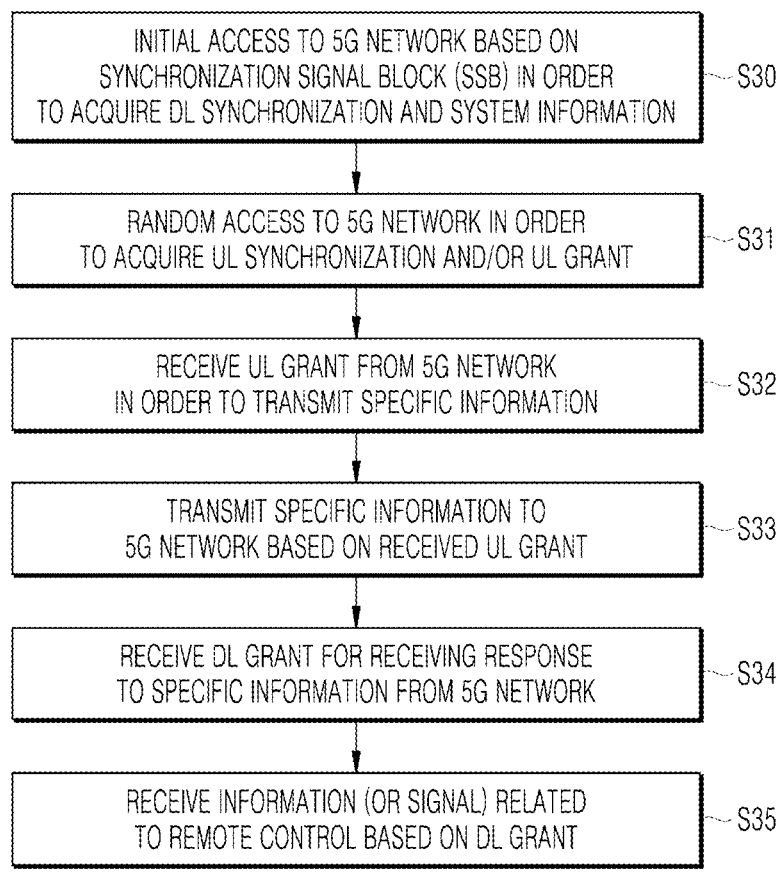
FIGS. 6 to 9 illustrate an example of an operation of a self-driving vehicle using 5G communication.

As illustrated in FIG. 6, the vehicle 200 including an autonomous driving module may perform an initial access process with the 5G network based on Synchronization Signal Block (SSB) for acquiring DL synchronization and system information (initial access step, S30).

The self-driving vehicle 200 may perform a random access process with the 5G network for UL synchronization acquisition and/or UL transmission (random access step, S31).

The self-driving vehicle 200 may receive the UL grant from the 5G network for transmitting specific information (UL grant receiving step, S32).

The self-driving vehicle 200 may transmit the specific information to the 5G network based on the UL grant (specific information transmission step, S33).

The self-driving vehicle 200 may receive the DL grant from the 5G network for receiving a response to the specific information (DL grant receiving step, S34).

The self-driving vehicle 200 may receive remote control related information (or a signal) from the 5G network based on the DL grant (remote control related information receiving step, S35).

A beam management (BM) process may be added to the initial access step, and a beam failure recovery process associated with Physical Random Access Channel (PRACH) transmission may be added to the random access step. QCL (Quasi Co-Located) relation may be added with respect to the beam reception direction of a Physical Downlink Control Channel (PDCCH) including the UL grant in the UL grant receiving step, and QCL relation may be added with respect to the beam transmission direction of the Physical Uplink Control Channel (PUCCH)/Physical Uplink Shared Channel (PUSCH) including specific information in the specific information transmission step. Further, a QCL relationship may be added to the DL grant reception step with respect to the beam receiving direction of the PDCCH including the DL grant.

Figure 7:
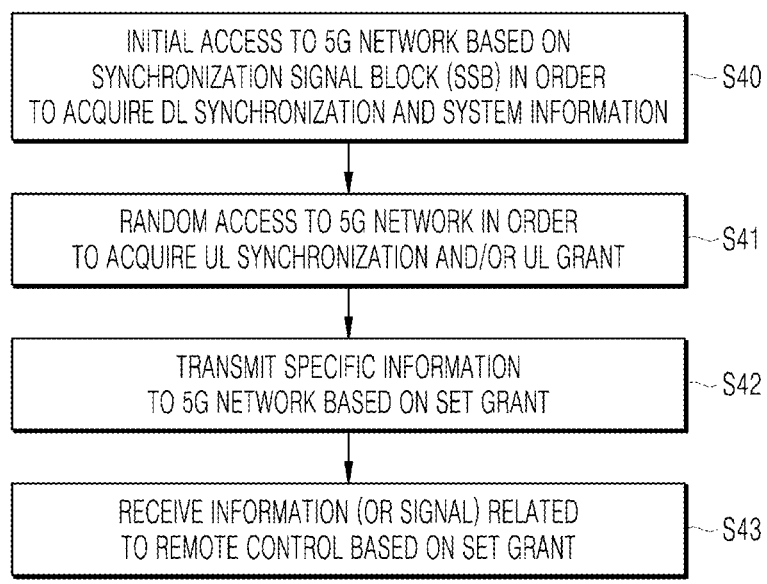

As illustrated in FIG. 7, the self-driving vehicle 200 may perform an initial access process with the 5G network based on SSB for acquiring DL synchronization and system information (initial access step, S40).

The self-driving vehicle 200 may perform a random access process with the 5G network for UL synchronization acquisition and/or UL transmission (random access step, S41).

The self-driving vehicle 200 may transmit specific information based on a configured grant to the 5G network (UL grant receiving step, S42). In other words, the self-driving vehicle 1000 may receive the configured grant instead of receiving the UL grant from the 5G network.

The self-driving vehicle 200 may receive the remote control related information (or a signal) from the 5G network based on the configured grant (remote control related information receiving step, S43).

Figure 8:
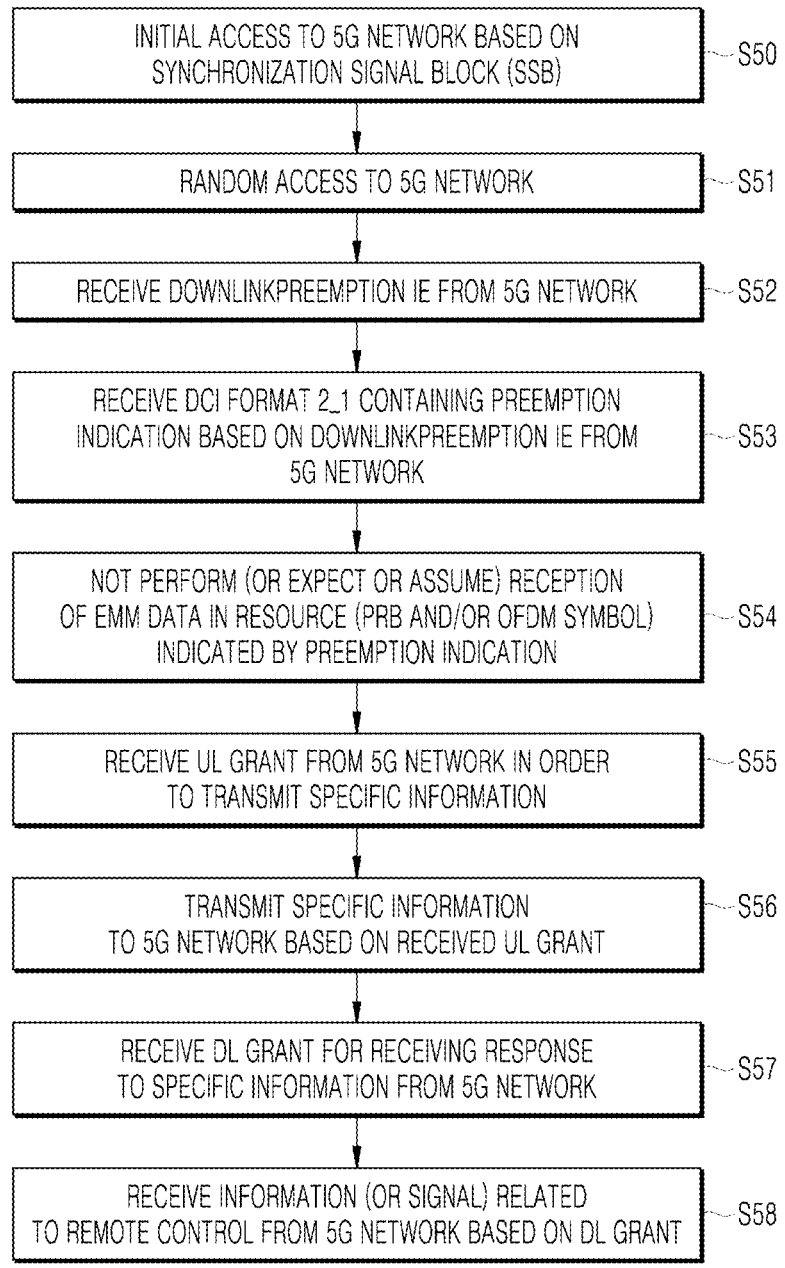

As illustrated in FIG. 8, the self-driving vehicle 200 may perform an initial access process with the 5G network based on SSB for acquiring DL synchronization and system information (initial access step, S50).

The self-driving vehicle 200 may perform a random access process with the 5G network for UL synchronization acquisition and/or UL transmission (random access step, S51).

In addition, the self-driving vehicle 200 may receive Downlink Preemption (DL) and Information Element (IE) from the 5G network (DL Preemption IE reception step, S52).

The self-driving vehicle 200 may receive DCI (Downlink Control Information) format 2_1 including preemption indication based on the DL preemption IE from the 5G network (DCI format 2_1 receiving step, S53).

The self-driving vehicle 200 may not perform (or expect or assume) the reception of eMBB data in the resource (PRB and/or OFDM symbol) indicated by the preemption indication (step of not receiving eMBB data, S54).

The self-driving vehicle 200 may receive the UL grant over the 5G network for transmitting specific information (UL grant receiving step, S55).

The self-driving vehicle 200 may transmit the specific information to the 5G network based on the UL grant (specific information transmission step, S56).

The self-driving vehicle 200 may receive the DL grant from the 5G network for receiving a response to the specific information (DL grant receiving step, S57).

The self-driving vehicle 200 may receive the remote control related information (or signal) from the 5G network based on the DL grant (remote control related information receiving step, S58).

Figure 9:
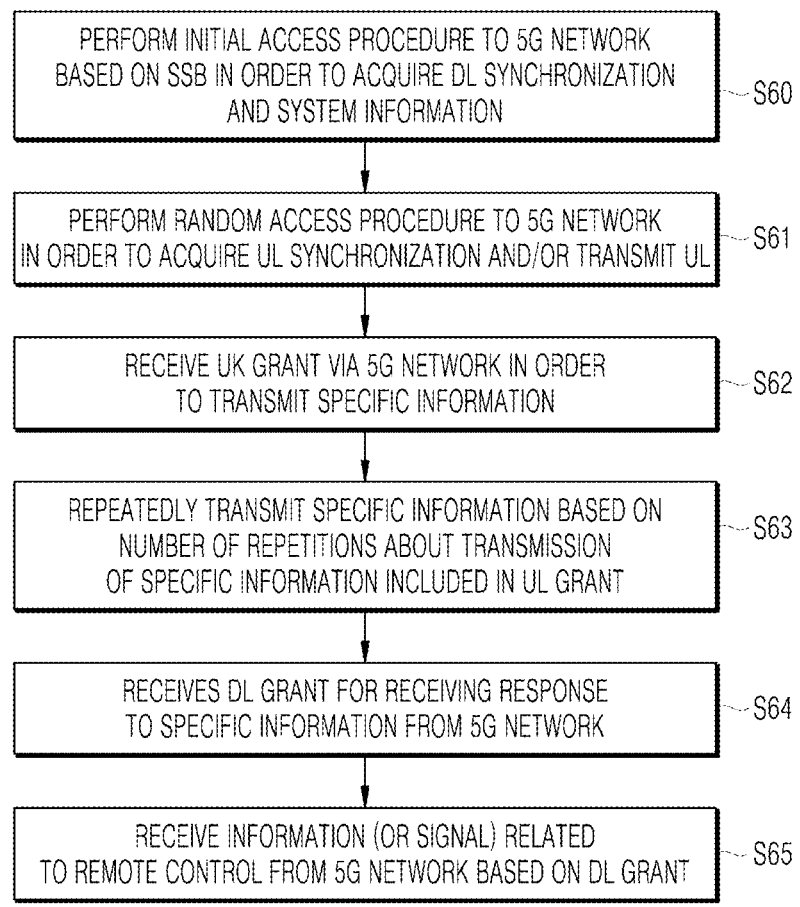

As illustrated in FIG. 9, the self-driving vehicle 200 may perform an initial access process with the 5G network based on SSB for acquiring DL synchronization and system information (initial access step, S60).

The self-driving vehicle 200 may perform a random access process with the 5G network for UL synchronization acquisition and/or UL transmission (random access step, S61).

The self-driving vehicle 200 may receive the UL grant over the 5G network for transmitting specific information (UL grant receiving step, S62).

When specific information is transmitted repeatedly, the UL grant may include information on the number of repetitions, and the specific information may be repeatedly transmitted based on information on the number of repetitions (specific information repetition transmission step, S63).

The self-driving vehicle 200 may transmit the specific information to the 5G network based on the UL grant.

Also, the repetitive transmission of specific information may be performed through frequency hopping, the first specific information may be transmitted in the first frequency resource, and the second specific information may be transmitted in the second frequency resource.

The specific information may be transmitted through Narrowband of Resource Block (6RB) and Resource Block (1RB).

The self-driving vehicle 200 may receive the DL grant from the 5G network for receiving a response to the specific information (DL grant receiving step, S64).

The self-driving vehicle 200 may receive the remote control related information (or signal) from the 5G network based on the DL grant (remote control related information receiving step, S65).

The above-described 5G communication technique may be applied in combination with the embodiment proposed in this specification, which will be described in FIG. 1 to FIG. 17, or supplemented to specify or clarify the technical feature of the embodiment proposed in this specification.

The image receiver 120 may receive an image acquired by photographing the inside of the vehicle from the image sensor 120-1. In the present embodiment, the image receiver 120 may receive a thermal image in the vehicle from the image sensor 120-1. That is, in the present embodiment, the image sensor 120-1 may be a camera and the controller 180 may acquire a human body thermal image using the camera. The camera may be configured to include a thermal sensor. The thermal sensor may sense light in an infrared region emitted from the human body to capture a thermal image. The camera may be implemented as a thermal infrared camera or a thermal infrared camera module, and an installation position is not limited. The thermal infrared camera or the thermal infrared camera module may include a lens, a thermal sensor, a filter, a convertor, and a processor and a memory required for thermal image processing, separately from the controller 180 and the storage 160 of the vehicle air conditioning control apparatus 100.

The user interface 130 may refer to a vehicle user interface. The user interface 130 is used for communication between the vehicle 200 and the vehicle user. The user interface 1300 may receive an input signal of the user, transmit the received input signal to the controller 180, and provide information held by the vehicle 200 to the user by the control of the controller 180. The user interface 130 may include a manipulator, an internal camera, a biosensor module, and a display, but is not limited thereto.

The manipulator 122 in the user interface 130 may be provided with a plurality of operation buttons (not illustrated) and may transmit a signal corresponding to an inputted button to the controller 180. This manipulator 122 may be configured with a sensor, button, or switch structure capable of recognizing a touch or pressing operation of the user. In the present embodiment, the manipulator may transmit a manipulation signal which is manipulated by a user to check or change various information related to the operation of the vehicle air conditioning control apparatus 100 displayed on the display, to the controller 180. Further, the manipulator may transmit a manipulation signal which is manipulated by a user to check or change various information related to the operation of the vehicle 200 other than air conditioning, to the controller 180.

Further, the display of the user interface 130 may display the operating state of the vehicle air conditioning control apparatus 100 under the control of the controller 180. According to an embodiment, the display 121 may form a layered structure with a touch pad so as to be configured as a touch screen. In this case, the display may also be used as a manipulator which inputs information by the touch of the user. For this purpose, the display 120 may be configured as a touch recognition display controller or various other input/output controllers. As an example, the touch recognition display controller may provide an output interface and an input interface between the device and the user. The touch recognition display controller may transmit and receive electrical signals to and from the controller 180. Also, the touch recognition display controller may display a visual output to the user, and the visual output may include text, graphics, images, video, and a combination thereof.

In the meantime, the user interface 130 may be included in the above-described vehicle user interface or include a vehicle user interface and the display may be included in an output interface of the vehicle user interface or include an output interface. Further, the modulator may be included in an input interface of the vehicle user interface or include an input interface.

The vehicle information receiver 140 may receive all information which may be acquired from the vehicle, such as vehicle driving information, vehicle inside information, or vehicle outside information. For example, the vehicle information receiver 140 may include vehicle driving information when the vehicle is driven, such as a vehicle speed or a steering angle, vehicle manipulation information such as window open/closed state and door open/closed state, and environment information of the inside/outside of the vehicle, such as a vehicle inside temperature or a vehicle outside temperature. That is, the vehicle information receiver 140 receives the vehicle information from the driving manipulation module, the vehicle driving module, and the operation module which have been described above to provide the vehicle information to the controller 180.

The air conditioning controller 150 controls the air conditioner of the vehicle under the control of the controller 180. That is, the air conditioning controller 150 receives a control signal of the controller 180 to drive the wind direction adjusting motor 150-1 and the wind volume adjusting motor 150-2 to adjust the wind direction and the wind volume. For example, in the present embodiment, the air conditioning controller 150 may adjust the wind direction by controlling a discharging angle using the wind direction adjusting motor equipped in the air conditioning discharging port in accordance with a control signal from the controller 180 based on the thermal comfort information of the passengers in the vehicle. Further, the air conditioning controller 150 performs the PID control to calculate a target duty ratio and transmit the calculated target duty ratio to the wind volume adjusting motor to adjust the wind volume. In this case, in the present embodiment, a gain value corresponding to the thermal comfort is calculated and the calculated gain value is used as a gain value for the PID control to adjust the wind volume.

The storage 160 may be set to store a human body recognizing module, a body temperature analysis module, and an air conditioning control module. Here, various modules may be implemented as software set to be loaded or unloaded in the storage 160 or implemented as an integrated circuit type hardware. The storage 160 may be configured to include a volatile memory and a non-volatile memory as a type of storage. Then, the nonvolatile memory may be used as a storage device. At least one software may be stored in the storage 160. The software may include an operating system, a system program, and various application programs. The storage 160 may be configured to store a human body detection module, a feature extraction module, a thermal comfort extraction module, and an air conditioning control module. Each module may be set to include an instruction set regarding each function which configures a thermal comfort based air conditioning method according to an exemplary embodiment of the present disclosure. Various logic circuits included in the controller 180 read the instruction set of various modules loaded in the storage 160 and the functions of the modules may be performed by the vehicle air conditioning control apparatus 100 during the executing process.

That is, the storage 160 may store various information required for the operation of the vehicle air conditioning control system 1. For example, in the storage 160, thermal image data for extracting the thermal comfort and vehicle information data may be stored.

Here, the storage 160 may include magnetic storage media or flash storage media, but the present disclosure is not limited thereto. The storage 160 may include an embedded memory and/or an external memory and also include a volatile memory such as a DRAM, an SRAM, or an SDRAM, a non-volatile memory such as one time programmable ROM (OTPROM), a PROM, an EPROM, an EEPROM, a mask ROM, a flash ROM, an NAND flash memory, or an NOR flash memory, a flash drive such as an SSD, a compact flash (CF) card, an SD card, a micro-SD card, a mini-SD card, an Xd card, or a memory stick, or a storage device such as a HDD.

The processor 170 may perform learning in conjunction with the controller 180, or may receive a learning result from the controller 180. In the present embodiment, the processor 170 may be provided outside the controller 180 as illustrated in FIG. 3, or may be provided in the controller 180 to operate like the controller 180, or may be provided in the server 300 of FIG. 2. Next, the processor 170 will be described in greater detail with reference to FIG. 10.

The controller 180 may acquire a thermal image in the vehicle using the image sensor 120-1 and acquire the thermal comfort information of the passengers in the vehicle using the thermal image. Further, the controller 180 may drive the wind direction adjusting motor 150-1 and the wind volume adjusting motor 150-2 based on the thermal comfort information of each passenger to control the air conditioning of the vehicle. That is, the controller 180 may be set to control the driving of the air conditioner in the vehicle based on information related to the vehicle air conditioning control apparatus 100 and sensed information collected through various sensors. Here, the human body thermal image information and the vehicle information may be included in the scope of the sensed information. In this case, the human body thermal image information may be based on a thermal image acquired through the thermal image camera (image sensor) equipped with a temperature sensor. The scope of the human body thermal image information may be set to include information related to the detected human body region, temperature information of a specific part of the human body region, that is, a skin temperature feature of a distal part of the body.

The controller 180, which is a kind of central processor, may operate the control software provided in the storage 160 in order to control the overall operation of the vehicle air conditioning system 1. The controller 180 may include any type of device capable of processing data, such as a processor. Here, the term "processor" may refer to a data processing device built in hardware, which includes physically structured circuits in order to perform functions represented as a code or instruction present in a program. Examples of the data processing device built in hardware may include microprocessors, central processing units (CPUs), processor cores, multiprocessors, application-specific integrated circuits (ASICs), digital signal processors (DSPs), digital signal processing devices (DSPDs), programmable logic devices (PLDs), processors, controllers, micro-controllers, and field programmable gate array (FPGA), but the present disclosure is not limited thereto.

In the present embodiment, the controller 180 may perform machine learning, such as deep learning, on the thermal comfort analysis of each passenger of the vehicle of the vehicle air conditioning control system 1 and vehicle air conditioning data in accordance with the thermal comfort to allow the vehicle air conditioning control system 1 to perform optimal vehicle air conditioning control and the storage 160 may store the data used for the machine learning and result data.

Deep learning, which is a subfield of machine learning, enables data-based learning through multiple layers. Deep learning may represent a set of machine learning algorithms that extract core data from a plurality of data sets as the number of layers increases.

Deep learning structures may include an artificial neural network (ANN). For example, the deep learning structure may include a deep neural network (DNN), such as a convolutional neural network (CNN), a recurrent neural network (RNN), and a deep belief network (DBN). The deep learning structure according to the present embodiment may use various structures well known in the art. For example, the deep learning structure according to the present disclosure may include a CNN, a RNN, and a DBN. The RNN is widely used in natural language processing, and can be effectively used to process time-series data that changes over time, and may construct an ANN structure by progressively extracting higher level features through multiple layers. A DBN includes a deep learning structure formed by stacking up multiple layers of a deep learning scheme, restricted Boltzmann machines (RBM). When a predetermined number of layers are constructed by repetition of such RBM learning, the DBN provided with the predetermined number of layers can be constructed. A CNN includes a model mimicking a human brain function, built under the assumption that when a person recognizes an object, the brain extracts the most basic features of the object and recognizes the object based on the results of complex processing in the brain.

Further, the artificial neural network may be trained by adjusting weights of connections between nodes (if necessary, adjusting bias values as well) so as to produce a desired output from a given input. Furthermore, the artificial neural network may continuously update the weight values through training. Furthermore, a method of back propagation or the like may be used in the learning of the artificial neural network.

That is, an artificial neural network may be installed in the vehicle air conditioning system 1, and the controller 180 may include an artificial neural network, for example, a deep neural network (DNN) such as a CNN, an RNN, and a DBN. Therefore, the controller 180 may train the deep neural network for the thermal comfort analysis of the passenger in the vehicle of the vehicle air conditioning control system 1 and the air conditioning control data in accordance with the thermal comfort analysis. As a machine learning method for such an artificial neural network, both unsupervised learning and supervised learning may be used. The controller 180 may control so as to update an artificial neural network structure after learning according to a setting.

In this embodiment, parameters for pre-trained deep neural network may be collected. In this case, a parameter for deep neural network learning may include thermal image data, human body region recognizing data of each passenger, skin temperature feature data, thermal comfort extraction data, and vehicle information data. Further, the parameter for deep neural network learning may include a voice instruction, an operation of the vehicle air conditioning control system 1 corresponding to the voice instruction, and user customized operation data. However, in the present embodiment, the parameters for deep neural network learning are not limited thereto. In the present embodiment, data used by an actual user may be collected in order to refine the learning model. That is, in the present embodiment, the user data may be inputted from the user through the vehicle transceiver 110 and the vehicle user interface 130. In the present embodiment, when the user data is received from the user, input data may be stored in the server and/or the memory regardless of the result of the learning model. That is, in the present embodiment, the vehicle air conditioning control system 1 stores data for thermal comfort analysis of the passenger in the vehicle in the server to configure big data and executes the deep learning at a server side to update the related parameter in the vehicle air conditioning control system 1, to be refined. However, in the present embodiment, the update may be performed by executing deep learning at the vehicle air conditioning control system or the edge side of the vehicle by itself. That is, in the present embodiment, at an initial setting of the vehicle air conditioning control system or an initial release of the vehicle, the deep learning parameter of a laboratory condition is embedded and is updated using data accumulated as the user drives the vehicles, that is, the user uses the air conditioning system of the vehicle. Therefore, in the present embodiment, the collected data may be labeled to obtain a result through map learning, and the result may be stored in the memory of the vehicle air conditioning control system to complete an evolving algorithm. That is, the vehicle air conditioning control system 1 may collect data for controlling vehicle air conditioning to generate a training data set, and may train the training data set through a machine learning algorithm to determine a trained model. In addition, the vehicle air conditioning control system may collect data used by the actual user and relearn the data in the server to generate a retrained model. Therefore, in the present embodiment, even after data is determined as a learned model, data may be continuously collected and learned by applying a machine learning model, and the performance may be improved by the learned model.

Figure 10:
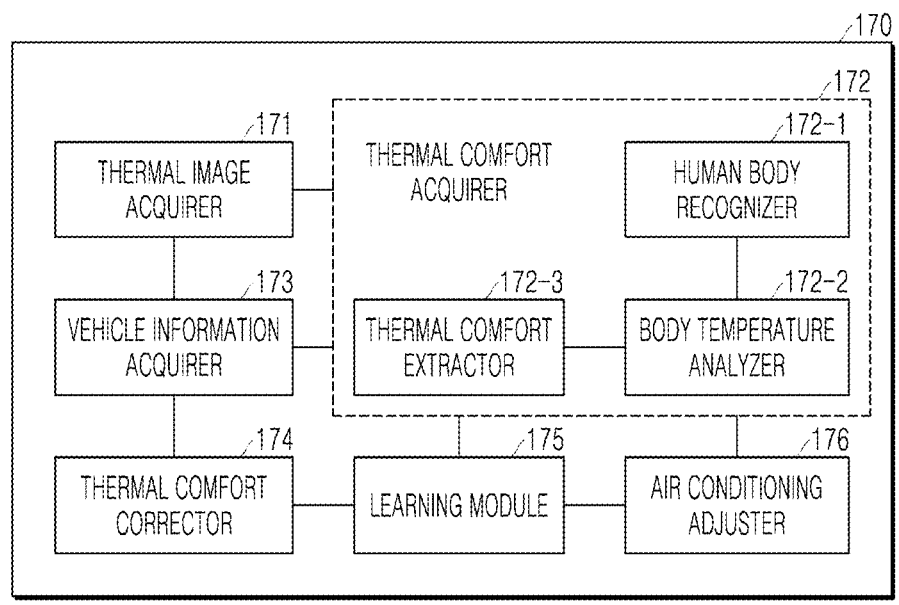
FIG. 10 is a block diagram schematically illustrating a processor of a vehicle air conditioning control method according to an embodiment of the present disclosure.

FIG. 10 is a block diagram schematically illustrating a processor of a vehicle air conditioning control method according to an embodiment of the present disclosure. In the following description, description of parts that are the same as those in FIG. 1 to FIG. 9 will be omitted.

Referring to FIG. 10, the processor 170 includes a thermal image acquirer 171, a thermal comfort acquirer 172, a vehicle information acquirer 173, a thermal comfort corrector 174, a learning module 175, and an air conditioning adjuster 176.

The thermal image acquirer 171 may acquire a thermal image in the vehicle using the image sensor 120-1. Further, the thermal image acquirer 171 may pre-process the thermal image. Here, the scope of the preprocessing may include preprocessing on raw data, extracting a body part in accordance with the human body detection, and preprocessing a body part. Specifically, the preprocessing process may include a noise removal process and an image brightness adjustment process. In the meantime, in the present embodiment, when a processor for preprocessing and a memory are equipped in the image sensor which photographs the thermal image in the vehicle, that is, in the camera, the camera or the camera module may perform the process of preprocessing the thermal image.

The thermal comfort acquirer 172 may acquire thermal comfort information of the passenger in the vehicle using the thermal image acquired by the thermal image acquirer 171. In this case, the thermal comfort acquirer 172 may include a human body recognizer 172-1, a body temperature analyzer 172-2, and a thermal comfort extractor 172-3.

The human body recognizer 172-1 may recognize a human body region of the passenger in the thermal image in the vehicle. That is, the human body recognizer 172-1 detects a human body region from the acquired thermal image and detects a body part. The human body recognizer 172-1 may detect a distal part such as hands or ears where many shunt vessels suitable to determine thermal comfort are distributed, among various body parts. That is, in the present embodiment, the thermal comfort of each passenger is determined by a temperature of the distal part of the body parts to control the air conditioning so that the thermal comfort of each passenger is more accurately determined to improve satisfaction for the air conditioning control. In this case, the distal part of the body part may refer to a part of an end portion of the human body such as a fingertip, an end of the ear, an end of a toe, and a forehead.

According to the embodiment of the present disclosure, various face recognition algorithms are not directly used, but are applied to detect a human body region. For example, the face recognition algorithm which is applied to detect the human body region may include a method of comparing an input image and a reference image stored in a database based on a geometric feature of the face and determining whether to match, an eigenfaces algorithm, a fisherfaces algorithm, a support vector machine (SVM) based algorithm, a method of recognizing a face using a neural network, a method of recognizing a face using a fuzzy and neural network, and a face recognition algorithm using wavelet and elastic matching. However, in the present embodiment, as compared with identification of the human body, it is necessary to detect the human body itself. Therefore, even though various human body recognition algorithms described above may be applied, a human body region may be detected by detecting a subject having a human's possible body temperature distribution.

That is, in the present embodiment, when a human body region is detected from the thermal image, various body parts, for example, a distal part such as hands or ears may be recognized through a human body learning process. As compared with recognition of a gesture by a shape of a finger, specifically, it is necessary to detect a region of the hand. Therefore, the hand region may be detected using human body skeleton information, rather than a gesture recognition algorithm of the related art.

In summary, the human body recognizer 172-1 may sequentially and separately detect the human body region and the body part or simultaneously detect the human body region and the body part. During this process, various algorithms for detecting the human body region and the body part as described above may be used. That is, the human body recognizer 172-1 may separate a distal part such as hands or ears from the human body region where a motion is captured, after removing a background from the acquired thermal image, using various algorithms.

The body temperature analyzer 172-2 may analyze a skin temperature feature using a temperature of the human body region. That is, the body temperature analyzer 172-2 extracts body temperature information of the body part and extracts a feature of the skin temperature of the body part using the body temperature information. Here, the scope of the feature of the skin temperature may include a feature vector of a skin temperature of the finger and a feature vector related to a temperature difference between the finger and the palm. Moreover, the scope of the feature of the skin temperature may include a size of a specific frequency region in a frequency-converted thermal image information and a feature vector of a skin temperature of the ear. That is, the body temperature analyzer 172-2 detects a temperature for every part of the human body and extracts a skin temperature feature using the detected temperature. For example, the body temperature analyzer 172-2 may extract the skin temperature feature of the distal part such as hands or ears where many shunt vessels are distributed in the human body based on the detected body part. In this case, the body temperature analyzer 172-2 may extract the skin temperature of the body part in accordance with expansion or contraction of the shunt vessel.

Figure 11:
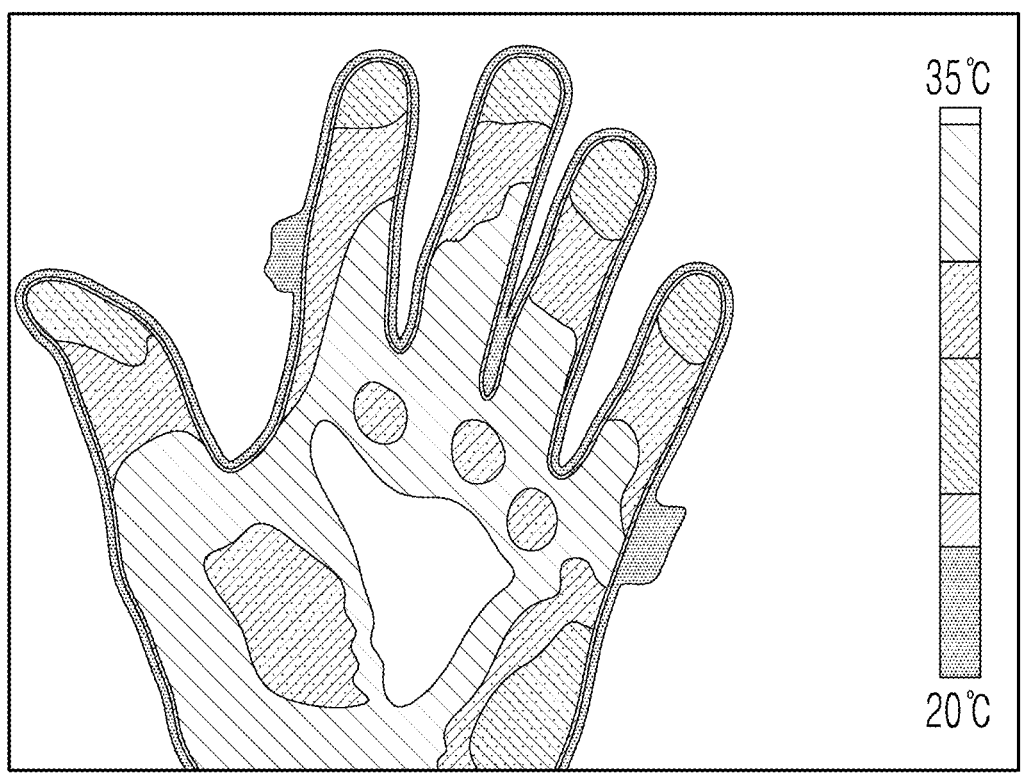
FIG. 11 is an exemplary diagram of a thermal image of a hand of a human body according to an embodiment of the present disclosure.

FIG. 11 is an exemplary diagram of a thermal image of a hand of a human body according to an embodiment of the present disclosure. Referring to FIG. 11, it is illustrated that the body temperature is distributed to be relatively low at the fingertip, as compared with the palm or the back of the hand. The thermal comfort of the human body may be easily estimated based on the body temperature feature of the fingertip.

Figure 12A:
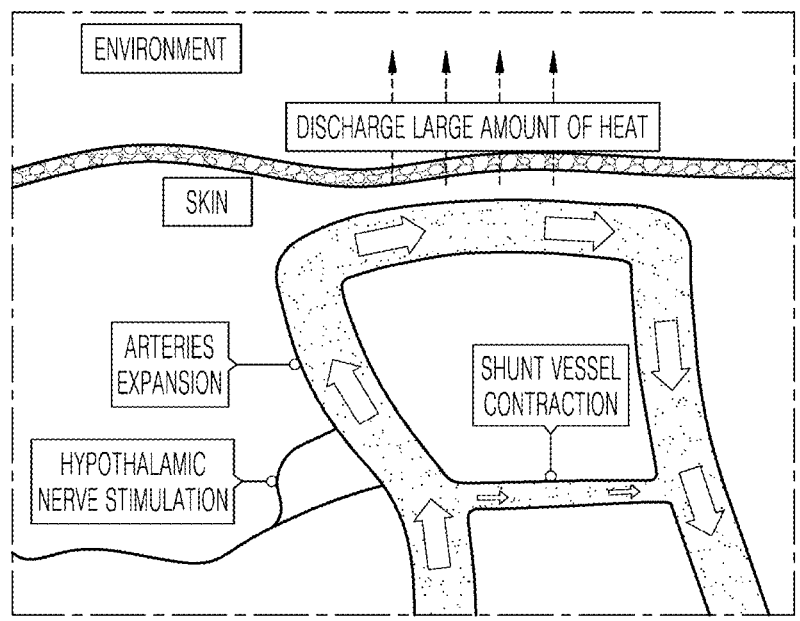
FIG. 12A is an exemplary diagram for explaining a body temperature change related to thermal comfort according to an embodiment of the present disclosure.
Figure 12B:
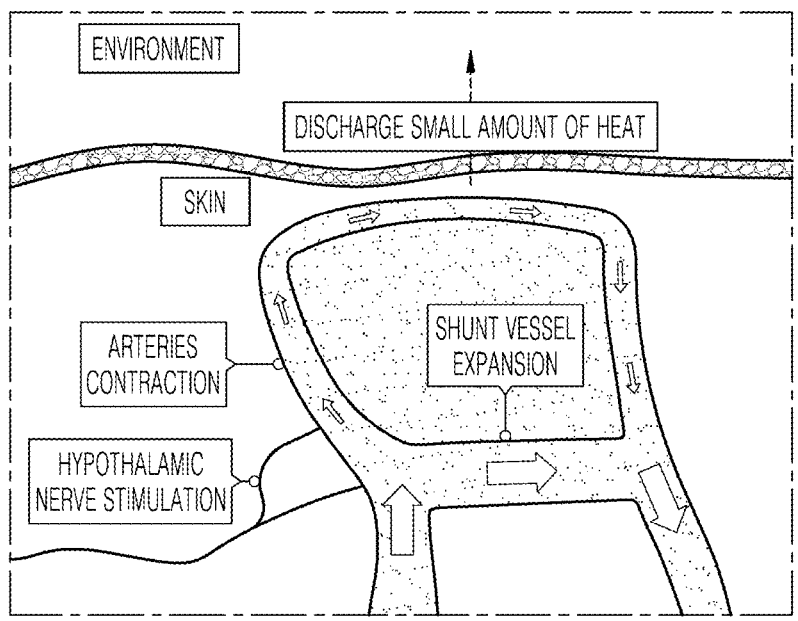
FIG. 12B is an exemplary diagram for explaining a body temperature change related to thermal comfort according to an embodiment of the present disclosure.

FIGS. 12A and 12B are exemplary diagrams for explaining a body temperature change related to thermal comfort according to an embodiment of the present disclosure. Referring to FIGS. 12A and 12B, capillaries are located directly under the skin and the shunt vessel connected to the capillaries is located far from the skin. The capillaries and the shunt vessel are controlled to contract and expand by hypothalamic nerve stimulation.

The shunt vessel is also referred to as arteriovenous anastomosis (AVA) and directly connects arteries and veins without passing through the capillaries. The shunt vessel is parallel to the capillaries so that a blood flow rate may be controlled by the interaction between the shunt vessel and the capillaries. For example, as a blood flow rate of the shunt vessel is increased, a blood flow rate flowing through the capillaries is reduced and in contrast, as the blood flow rate of the shunt vessel is reduced, the blood flow rate flowing through the capillaries is increased.

The number of arteriovenous anastomosis in the hand and the finger is much larger than the number of the rest of the body surface and when the arteriovenous anastomosis is open and then closed, the temperature of the hand may vary in a wide range of temperatures. The arteriovenous anastomosis is mainly controlled by a signal of the hypothalamus so that the operation of the arteriovenous anastomosis is indicative of overall body thermal state.

Blood usually supplies oxygen and nutrients to cells through the capillaries and accepts waste products. However, in the shunt vessel, the exchange of the materials is omitted.

The capillaries are located to be close to the skin surface, but the shunt vessel is located deep in the skin. Therefore, the range of the temperature change due to the blood flow rate of the capillaries which are more affected by the external temperature is larger than that of the shunt vessel.

Referring to FIG. 12A again, when the body temperature rises due to the temperature rise, the blood flow rate of the shunt vessel is reduced to increase heat release to the outside so that the blood flow rate of the capillaries is increased and the heat release to the outside is increased in accordance with the increase of the blood flow rate. Therefore, the body temperature rise is suppressed.

Referring to FIG. 12B again, when the body temperature is lowered due to the drop in the temperature, in order to reduce heat loss to the outside, the blood flow rate of the shunt vessel is increased to reduce the blood flow rate of the capillaries. Therefore, the heat loss released to the outside is reduced so that the body temperature drop is suppressed.

When there is a difference between a temperature at which the human body feels comfortable and a temperature in an air conditioning space, the shunt vessel is involved to adjust the body temperature. When it is necessary to adjust a large amount of blood flow to adjust the body temperature, the human body may feel discomfort, instead of the thermal comfort. In this case, a sign that the thermal comfort is broken may be represented in the hand of the human body where the shunt vessels are intensively distributed. Further, as a sign of a thermally discomfort emotion felt by the human body, the temperature of the hand may be higher or lower than the other parts.

As described above, the shunt vessel may be directly involved to adjust the body temperature in accordance with a warm feeling and a cold feeling. Therefore, when the temperature of the air conditioning space rises or drops such that the personal thermal comfort is broken due to insufficient or excessive air conditioning, it is estimated whether the thermal comfort of the human body is maintained based on the feature of the skin temperature of the hand where many shunt vessels are distributed.

Figure 13:
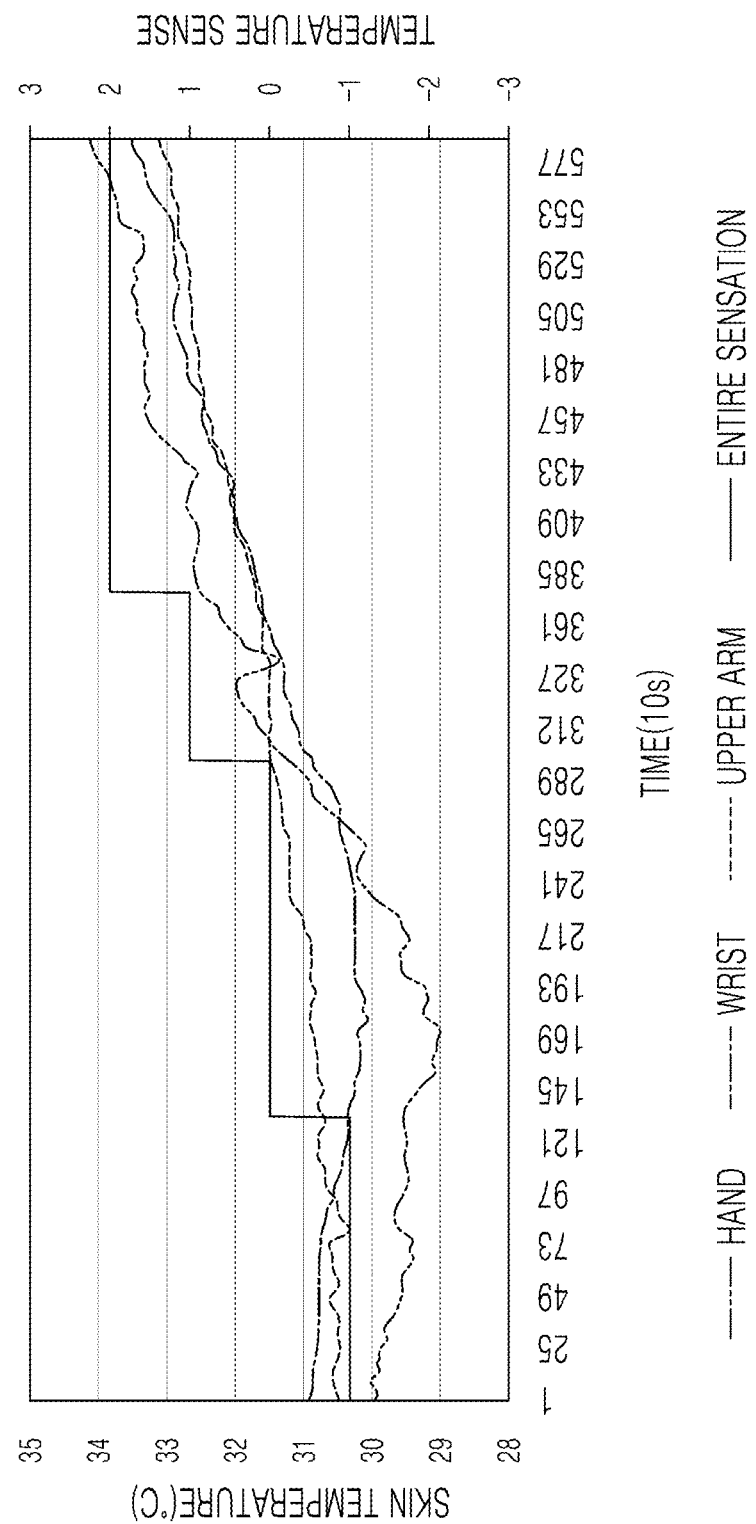
FIG. 13 is a graph illustrating a relationship between a skin temperature measured in a surrounding part including a hand and a thermal sense.

FIG. 13 is a graph illustrating a relationship between a skin temperature measured in a surrounding part including a hand and a temperature sense according to an embodiment of the present disclosure. Referring to FIG. 13, changes in the skin temperature of a hand, a wrist, and an upper arm are illustrated and an overall sense felt by the human body, that is, the thermal comfort is illustrated. The feature of the skin temperature of the hand has a broader temperature change than the other parts. Therefore, when the body temperature change is sensed through the thermal image, if the temperature change is sensed by pointing to the skin of the hand, the body temperature change may be easily sensed.

Therefore, in the present embodiment, the thermal comfort may be extracted with the temperature of the distal part and a temperature difference between the distal part and other body parts as parameters. That is, the thermal comfort is extracted with the temperature of the distal part to improve the accuracy. Further, the present embodiment relates to the air conditioning control in the vehicle so that since in the vehicle, the air conditioning discharging part is close to the user, so that it is more sensitive to the temperature change. Therefore, it is necessary to more accurately detect the temperature. Therefore, it is very important to extract the thermal comfort by detecting a temperature of the distal part and control the air conditioning based on the thermal comfort.

The thermal comfort extractor 172-3 may extract the thermal comfort of the passengers based on the skin temperature feature analysis result. That is, the thermal comfort extractor 172-3 estimates the thermal comfort of the human body through the analysis of the feature of the skin temperature and extracts the thermal comfort information based on the estimation. In the present embodiment, the thermal comfort estimation is estimation about whether the state felt by the human body is comfort. For example, when a temperature of a body part which is exposed to the outside without being covered with the clothing, among the body parts, is lower than that of a part covered with the clothing, the thermal comfort extractor 172-3 may estimate that it is not thermally comfort because the detected human body feels cold. In contrast, when a temperature of a body part which is exposed to the outside is higher than that of the part covered with the clothing, the thermal comfort extractor 172-3 may estimate that it is not thermally comfort because the detected human body feels hot.

Further, the thermal comfort extractor 172-3 may extract thermal comfort information in accordance with estimation. In the present embodiment, the thermal comfort may be extracted as numerical information. For example, a result of estimating the thermal comfort is thermal comfort information and may be extracted by number, like PMV, even though a predicted mean vote (PMV) is not directly calculated.

As elements which affect the thermal comfort of the human body in the thermal environment, an air temperature in the vehicle, a mean radiant temperature (MRT), an air velocity, and a humidity are provided and as a personal element, a metabolism and clothing quantity (do value) are provided.

The thermal comfort may refer to a state of the mind indicating a satisfaction in a warm environment. As a representative evaluation reference for the air conditioning comfort, a predicted mean vote (PMV) and a predicted percentage dissatisfied (PPD) are provided.

PMV may be calculated based on (1) an air temperature, (2) a partial water vapor pressure, (3) a mean radiant temperature, (4) a relative air velocity, (5) a thermal resistance, and (6) a metabolic rate.

$$PMV=[0.303 \exp(-0.036M)+0.028]L$$

Here, M refers to a body heating value and L is a function of a thermal load and caloric value of the human body.

The PMV may be used to predict a clothing quantity from which the comfort may be acquired under various environmental conditions or predict a comfort environmental condition under any clothing condition. In the temperature condition, the reaction of human is represented by seven reference values (+3: hot, +2: warm, +1: slightly warm, 0: neutral, −1: slightly cool, −2: cool, and −3: cold). When the PMV has a value between −0.5 and +0.5, it is considered that a desirable thermal condition is built.

PPD represents thermal dissatisfaction that feels hot or cold under the same environment with a percentage of the total population. A predicted dissatisfaction of people for a thermal environment at a specific point is known and is calculated by the following equation.

$$PPD=100-95e^{-(0.03353PMV^4+0.2179PMV^2)}$$

Further, there is a contact cold/warm sensation of a contact associated with a type of a fabric of the clothing. The sensation is a sense which feels cold or worm at the moment of touching the fabric. This is a phenomenon that the heat is momentarily transferred from a warm hand to the fabric and when a lot of heat is moved, the human body feels cold. When the temperature of the fabric is maintained at the same temperature as the room temperature, the lower the room temperature, the more the heat moves from the hand to the fabric. Therefore, the heat of the hand is lost so that the human body feels cold. When the fabric contains moisture or when a surface of the fabric is smooth, or when the tissue of the fabric is dense, an amount of heat transfer is large. When there is much hair on the surface of the fabric, the amount of heat transfer is small. In summer, products made of textiles (hemp fibers) with high thermal conductivity are preferred.

As a world's representative standards related to the thermal environments, there are ASHRAE (American Society of Heating, Refrigerating and Air-conditioning Engineers) 55 and ISO (International Organization for Standardization) 7730. The ASHRAE 55 and ISO 7730 are established and revised to implement high thermal comfort based on the effective temperature and PMV, respectively.

In ISO 7730, an incentive value of a thermal comfort region with respect to a warm sense/cold sense of the entire body is represented in association with PMV and PPD. PPD is a percentage of people having dissatisfaction or discomfort for the thermal environment.

However, it is complex to calculate the thermal comfort using the PMV for the space air conditioning and it is not easily permitted to accurately measure a factor required to calculate the thermal comfort with limited equipment. Therefore, a countermeasure to estimate the thermal comfort is necessary.

The thermal infrared image representing the entire human body represents a simple body temperature distribution so that it is difficult to estimate the thermal comfort with the thermal infrared image which is not processed.

According to the thermal comfort based air conditioning method and the air conditioner using the same according to the embodiment of the present disclosure, the thermal comfort which is felt by the human body may be estimated by an artificial intelligence model trained by learning using an artificial intelligence algorithm.

That is, in the present embodiment, the thermal comfort acquirer 172 may acquire thermal comfort information of the passengers in the vehicle using one or more of a first deep neural network model and a second deep neural network model which are trained in advance to extract the thermal comfort of the human body by analyzing the skin temperature feature. In this case, the first deep neural network model may be trained to extract a skin temperature based on at least one of a finger skin temperature, a skin temperature difference between the finger and the palm, an ear skin temperature, and a size of a specific frequency region and obtain the thermal comfort information of the human body based on the skin temperature. Further, the second deep neural network model may be trained to extract a skin temperature based on at least one of thermal resistance information depending on the clothing wearing state of the passenger and temperature difference information in accordance with a position of a seat in the vehicle and acquire thermal comfort information of the human body based on the skin temperature.

Figure 14:
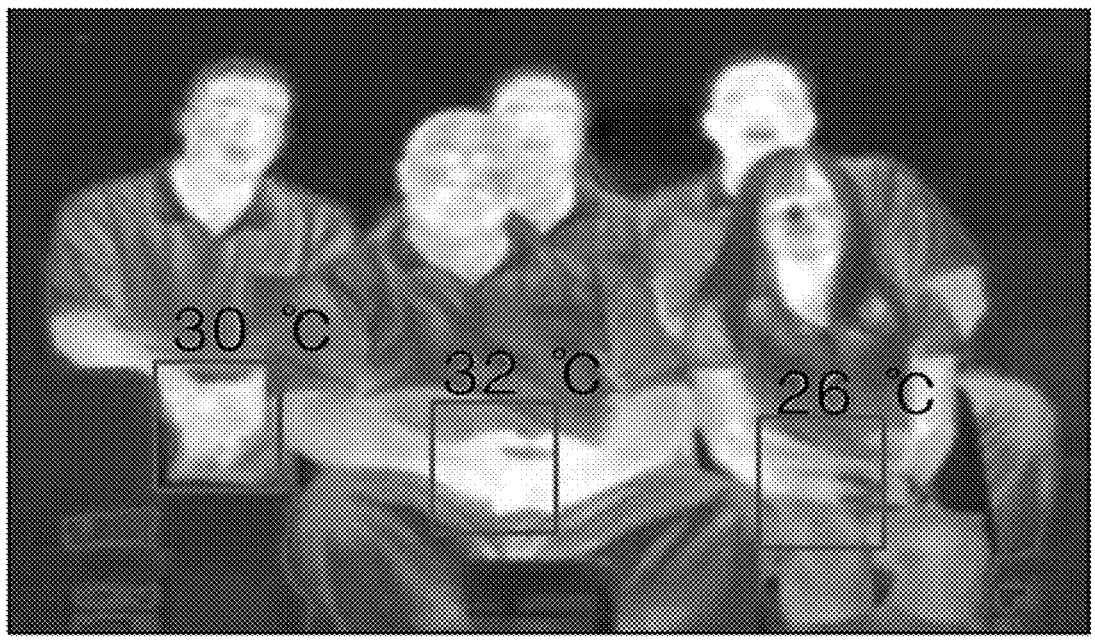
FIG. 14 is a view for explaining the sensing of a distal part of a human body of a passenger of the vehicle according to an embodiment of the present disclosure.

FIG. 14 is a view for explaining the sensing of a distal part of a human body of a passenger of the vehicle according to an embodiment of the present disclosure. Referring to FIG. 14, in the present embodiment, thermal images of a user or other passengers who are loaded in the vehicle are acquired to analyze the body temperature of a distal part thereof and then the thermal comfort is extracted. That is, in the present embodiment, the thermal resistance information is analyzed depending on the clothing wearing state of the passenger using the PMV. Further, the thermal comfort of the passengers may be extracted not only using the PPD, but also the vehicle information such as temperature difference information in accordance with the seat position in the vehicle. In this case, in the present embodiment, for example, the driver holds a steering wheel unlike other passengers, so that the temperature felt by the finger may vary. Further, the distance from the air conditioning discharging port may vary depending on the position of the driver and the passengers so that the temperature may vary by the distance. Therefore, when the characteristic information is reflected to extract the thermal comfort, a percentage of reflecting the skin temperature may vary.

The vehicle information acquirer 173 acquires vehicle information. In this case, the vehicle information may include at least one of vehicle internal environment sensing information, vehicle external environment sensing information, and vehicle control sensing information. The present embodiment relates to the air conditioning control in the vehicle, which is different from the air conditioning control in the inside of a building. For example, the vehicle is largely affected by the temperature change of the outside and also largely affected by the rapid and frequent change in the driving environment (for example, window open/close, door open/close, or sudden stop). Further, the distance from the air conditioning discharging port may vary depending on the seated position of the user or other passengers and at a closer distance than the air conditioning discharging port in a general indoor, the discharged air flow is encountered. Accordingly, it is desirable to extract the thermal comfort of the passengers by reflecting the characteristic of the vehicle so that vehicle information which may influence on the thermal comfort may be acquired.

The thermal comfort corrector 174 may correct the thermal comfort information of the passengers in the vehicle acquired using the thermal infrared image, based on the vehicle information. For example, when the window of the vehicle is open so that an event in the vehicle occurs, the thermal comfort information is corrected by reflecting the distance from the air conditioning discharging port or a temperature of the seat. In this case, in the present embodiment, the thermal comfort corrector 174 corrects the thermal comfort information of the passengers in the vehicle using a third deep neural network model which is trained in advance to analyze the vehicle information to extract a changed value of the thermal comfort information. In this case, the third deep neural network model may be trained to extract the changed value of the thermal comfort information of the human body based on at least one of vehicle internal environment sensing information, vehicle external environmental sensing information, and vehicle control sensing information and correct the thermal comfort information of the human body based on the changed value.

Figure 15:
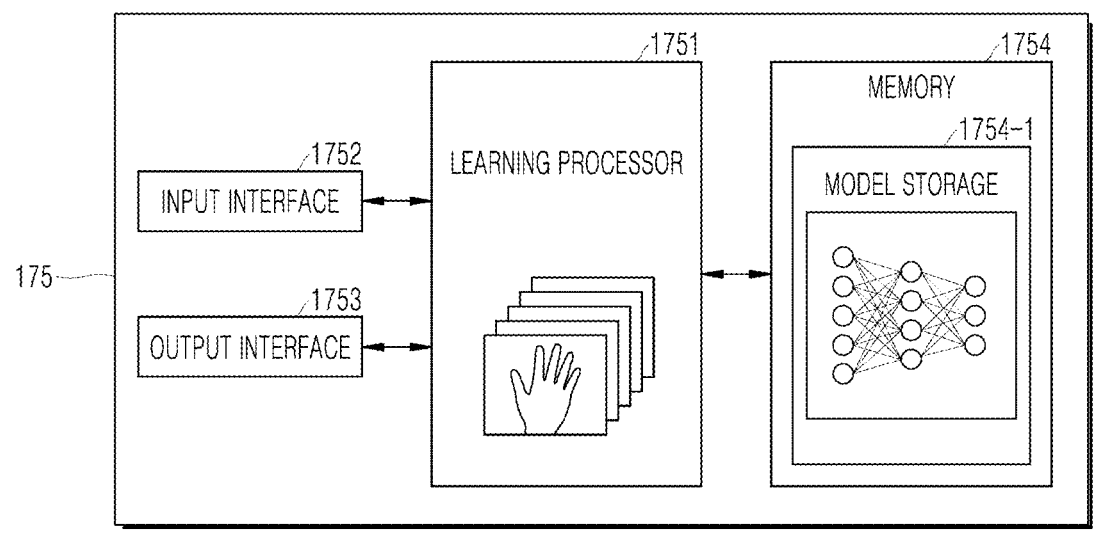
FIG. 15 is a block diagram schematically illustrating a learning module of a vehicle air conditioning control method according to an embodiment of the present disclosure.

FIG. 15 is a block diagram schematically illustrating a learning module of a vehicle air conditioning control method according to an embodiment of the present disclosure. In the following description, description of parts that are the same as those in FIG. 1 to FIG. 14 will be omitted.

First, in the present embodiment, the thermal comfort may be estimated based on a temperature and a humidity measured by a sensor, for example, a temperature sensor and a humidity sensor and a direction and a strength of an air flow set in the air conditioner in the vehicle in addition to the skin temperature feature of a body part extracted through the processes of acquiring body thermal image, preprocessing the thermal image, extracting the body part from the thermal image, and extracting a skin temperature feature of the body part. Here, the temperature, the humidity, and the air flow may correspond to thermal equilibrium factors related to the PMV. The temperature, the humidity, and the air flow may be reflected to the skin temperature feature to be represented. However, it is difficult to reflect the temperature, the humidity, and the air flow in a short time, so that the temperature, the humidity, and the air flow may be directly used to estimate the thermal comfort. When the thermal comfort is estimated, it is considered that the temperature, the humidity, and the air flow, and values of the direction and the strength of the air flow is changed from a primary set value of the direction and the strength of the air flow set using the learned model by the vehicle air conditioning control apparatus 100 to a secondary set value set by the user. For example, depending on how the primary set value of the direction and the strength of the air flow is changed in the secondary setting by the user, the direction and the strength of the air flow by which the thermal comfort of the user is maintained may be searched.

That is, in the present embodiment, the air conditioning is controlled in the vehicle air conditioning control system 1 using the artificial intelligence algorithm. Specifically, a step of extracting a skin temperature feature of a body part and estimating a thermal comfort based on the skin temperature feature, a step of estimating the thermal comfort based on sensing information and the body temperature feature, and a step of correcting the thermal comfort based on the vehicle information may be performed by the artificial intelligence (AI) model, for example, a deep learning model which is trained using learning data in accordance with an artificial intelligence algorithm.

Referring to FIG. 15, the learning module 175 may include a learning processor 1751, an input interface 1752, an output interface 1753, and a memory 1754. The learning module 175 may refer to an apparatus, a system, or a server that trains an artificial neural network using a machine learning algorithm or uses a trained artificial neural network. Here, the learning module 175 may include a plurality of servers to perform distributed processing, or may be defined as a 5G network. In this case, the learning module 175 is included as a part of a component of the vehicle air conditioning control system 1 to perform at least a part of the AI processing.

The input interface 1752 may receive thermal image data acquired from an image sensor, human body region recognition data of each passenger through the thermal image, skin temperature feature analysis data (finger skin temperature data, skin temperature difference data between finger and palm, ear skin temperature data, and size data of a specific frequency region) based on the temperature of the human body region, thermal comfort extraction data (thermal resistance data in accordance with clothing wearing state, temperature difference data in accordance with a seat position in the vehicle, or vehicle information data) as input data.

The learning processor 1751 may apply the received input data to the learning model for extracting control data for extracting vehicle air conditioning control data. The learning model may include a first deep neural network model and a second deep neural network model which are trained in advance to extract the thermal comfort of the human body by analyzing the skin temperature feature and a third deep neural network model which is trained in advance to extract a changed value of the thermal comfort data by analyzing the vehicle information. The learning processor 1751 may train the artificial neural network using the training data. The learning model may be used in a state of being mounted on the AI server (20 of FIG. 1) of the artificial neural network, or may be used in a state of being mounted on the external device.

The output interface 1753 may output thermal comfort data of each passenger in the vehicle and air conditioning control data (wind volume adjusting motor control data and wind direction adjusting motor control data) in accordance with the thermal comfort from the learning model.

The memory 1754 may include a model storage 1754-1. The model storage 1754-1 may store a model (or an artificial neural network) learning or learned via the learning processor 1751. The learning model may be implemented as hardware, software, or a combination of hardware and software. When a portion or the entirety of the learning model is implemented as software, one or more instructions, which constitute the learning model, may be stored in the memory 1754.

Further, referring to FIG. 15, a process of training an artificial intelligence model including a labeling method using a configuration of a learning image, a structure of an artificial neural network which performs the deep learning, and thermal comfort information is schematically illustrated. As learning image, a thermal image including the skin temperature information of the body part may be used. The server may collect user log data of the thermal image acquired from the air conditioner which is used by the user and other passengers as learning image. The thermal image illustrated in FIG. 15 is a hand, but the present embodiment is not limited to the hand. The thermal image in which the human body is represented by the human body searching may be used as the learning image and a thermal image cropped for every body part by recognizing the body part may be used to extract a skin temperature feature. As described above, the user log data and the thermal image are subjected to a data mining process to be used as the learning image. The thermal image may be input to a model which learns with an artificial intelligence algorithm, for example, an artificial neural network which performs the deep learning. The input thermal image passes through an input layer, a hidden layer, and an output layer to extract a feature which becomes a basis for estimating the thermal comfort. Further, when the thermal comfort information is given by the labeling, the artificial neural network compares and analyzes the extracted skin temperature feature for every body part and the thermal comfort information to perform the learning using the learning thermal image. Therefore, the artificial neural network may gradually complete the structure of the hidden layer which allows the labelled thermal comfort information to be estimated.

The artificial neural network may learn by weighting the skin temperature of a body part in which many shunt vessels are distributed, a difference between the skin temperature and a skin temperature of the other part, for example, a finger skin temperature, a skin temperature difference between the finger and the palm, an ear skin temperature, and a power of a specific frequency region of the skin temperature on a frequency domain. Further, the artificial neural network may learn the change of the thermal comfort based on the change of the skin temperature of a bare skin exposed to the outside, depending on a type of the clothing, such as sleeveless, short sleeves, and long sleeves.

Further, the artificial neural network may learn the thermal comfort state of the user using information about direct control of an air conditioner of the user using a remote controller in accordance with distribution of the skin temperature of the user based on the thermal image while executing the air conditioner. That is, in a thermal comfort information estimating scenario of the artificial neural network, not only the thermal image used as an input, but also a feedback of the user is used for the learning. For example, when the user opens the window of the vehicle and then closes the window, the user may want more powerful cooling. In this case, the artificial neural network may learn by weighting a situation in which the user adjusts the temperature using a remoted controller. As an embodiment for the learning, when it is recognized that it is hot through the measured external temperature information, the artificial neural network may weight to find out the thermal comfort pattern of the user represented in accordance with the external temperature information.

The air conditioning adjuster 176 controls the air conditioning of the vehicle based on the thermal comfort information of each passenger. That is, the air conditioning adjuster 176 serves to control the operation of the air conditioner, for example, the temperature and the humidity of the air flow, a strength and a direction of the air flow, based on the extracted thermal comfort information of the human body. Therefore, the air conditioning adjuster 176 may control the wind direction adjusting motor 150-1 and the wind volume adjusting motor 150-2 based on the thermal comfort information of the human body of each passenger. For example, when the human body feels cold or hot, the air conditioning may be controlled to control the temperature, the humidity, the strength and the direction of the air flow to raise or lower the temperature. That is, the air conditioning adjuster 176 identifies a thermal comfort index calculated based on the thermal comfort information of each passenger and detects a passenger having a thermal comfort index which is equal to or lower than a reference value, among the passenger in the vehicle. The air conditioning adjuster 176 may identify an air conditioning discharging port which is located in a predetermined distance from a passenger having a thermal comfort index which is equal to or lower than the reference value. The air conditioning adjuster 176 may generate a control signal of the wind direction adjusting motor 150-1 and the wind volume adjusting motor 150-2 to adjust the wind direction and the wind volume of the identified air conditioning discharging port.

That is, the air conditioning adjuster 176 controls a discharging angle using the wind direction adjusting motor equipped in the air conditioning discharging port to adjust the air direction. Further, the air conditioning adjuster 176 performs the PID control to calculate a target duty ratio and transmit the calculated target duty ratio to the wind volume adjusting motor to adjust the wind volume. In this case, the air conditioning adjuster 176 may calculate a gain value corresponding to the thermal comfort and use the calculated gain value as a gain value of the PID control.

In the present embodiment, the air conditioning adjuster 176 may extract the thermal comfort using information about the vehicle air conditioning control apparatus 100, sensed information collected by the sensors, as well as the skin temperature feature. The scope of the sensed information may include the temperature, the humidity, direction and strength information of the air flow set in each air conditioning port. In this case, the temperature may include an indoor temperature and an outdoor temperature and the outside temperature may be related to the weather of the corresponding date. A solar radiation quantity may be indirectly estimated by the outdoor temperature. Further, on a day with a large radiation quantity, the difference between the indoor temperature and the outdoor temperature is large and the cooling power of the vehicle air conditioning control device 100 needs to be increased.

As described above, according to various embodiments of the present disclosure, an air conditioning control method which estimates the thermal comfort of the human body using the thermal image and satisfies the thermal comfort for every person based on the extracted thermal comfort information in accordance with the estimation may be performed. Further, the discomfort generated due to the hot or cold by the excessive or insufficient air conditioning control may be prevented. Further, a state in which the individual feels the thermal comfort may be maintained by the air conditioning control.

Figure 16:
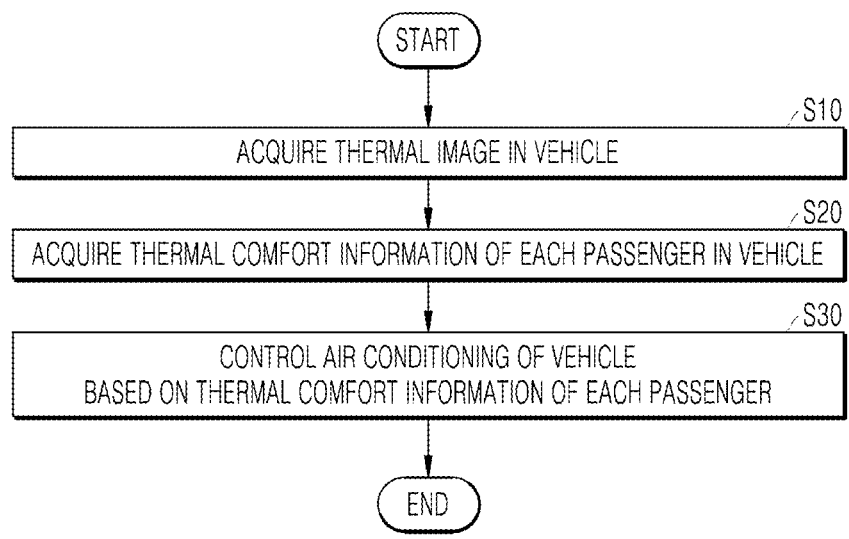
FIG. 16 is a flowchart schematically illustrating a vehicle air conditioning control method according to an exemplary embodiment of the present disclosure.
Figure 17:
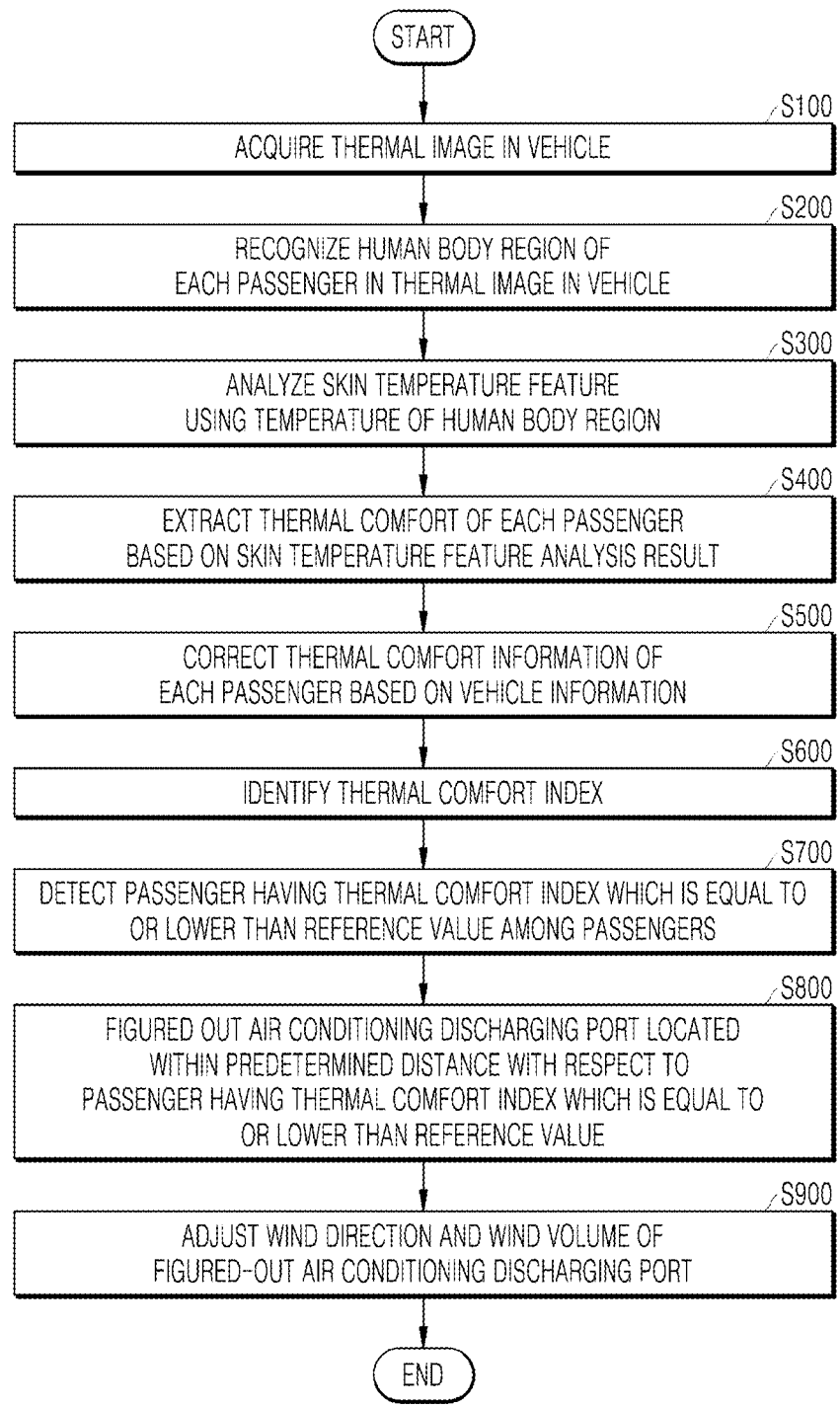
FIG. 17 is a flowchart more specifically illustrating a vehicle air conditioning control method according to an exemplary embodiment of the present disclosure.

FIG. 16 is a flowchart schematically illustrating a vehicle air conditioning method according to an exemplary embodiment of the present disclosure; and FIG. 17 is a flowchart more specifically illustrating a vehicle air conditioning method according to an exemplary embodiment of the present disclosure. In the following description, description of parts that are the same as those in FIG. 1 to FIG. 15 will be omitted.

Referring to FIG. 16, in step S10, the vehicle air conditioning control apparatus 100 acquires a thermal image in the vehicle using an image sensor 120-1. The vehicle air conditioning control apparatus 100 receives an image acquired by photographing the inside of the vehicle from the image sensor. That is, in the present embodiment, the vehicle air conditioning control apparatus 100 acquires a human body thermal image from a camera including a temperature sensor. That is, the vehicle air conditioning control apparatus 100 may acquire the thermal image captured by sensing light in an infrared ray region emitted from the human body.

In step S20, the vehicle air conditioning control apparatus 100 acquires thermal comfort information of each passenger in the vehicle using the thermal image. That is, in the present embodiment, the vehicle air conditioning control apparatus 100 may acquire thermal comfort information for controlling the driving of the air conditioner in the vehicle based on information about the air conditioner and sensed information collected by various sensors. Here, the human body thermal image information and the vehicle information may be included in the scope of the sensed information. In this case, the human body thermal image information may be based on a thermal image acquired through the thermal image camera (image sensor) equipped with a temperature sensor. Information about the detected body region, temperature information of a specific part of the human body region, that is, skin temperature feature of a distal part of the human body may be included in the scope of the human body thermal image information.

In step S30, the vehicle air conditioning control apparatus 100 controls the air conditioning of the vehicle based on the thermal comfort information of each passenger. That is, the vehicle air conditioning control apparatus 100 may drive the wind direction adjusting motor 150-1 and the wind volume adjusting motor 150-2 based on the thermal comfort information to adjust the wind direction and the wind volume. For example, in the present embodiment, the vehicle air conditioning control apparatus 100 may adjust the wind direction by controlling a discharging angle using the wind direction adjusting motor equipped in the air conditioning discharging port based on the thermal comfort information of the passengers in the vehicle. Further, the vehicle air conditioning control apparatus 100 performs the PID control to calculate a target duty ratio and transmit the calculated target duty ratio to the wind volume adjusting motor to adjust the wind volume. In this case, in the present embodiment, the vehicle air conditioning control apparatus 100 calculates a gain value corresponding to the thermal comfort and uses the calculated gain value as a gain value for the PID control to adjust the wind volume.

The control method of the vehicle air conditioning control apparatus 100 will be described in more detail with reference to FIG. 17. In step S100, the vehicle air conditioning control apparatus 100 acquires a thermal image in the vehicle. The vehicle air conditioning control apparatus 100 acquires the thermal image in the vehicle using the image sensor and preprocesses the thermal image. Here, the scope of the preprocessing may include preprocessing on raw data, extracting a body part in accordance with the human body detection, and preprocessing a body part. Specifically, the preprocessing process may include a noise removal process and an image brightness adjustment process.

In step S200, the vehicle air conditioning control apparatus 100 recognizes the human body region of each passenger in the thermal image in the vehicle. The vehicle air conditioning control apparatus 100 may recognize a human body region of the passenger in the thermal image in the vehicle. That is, the vehicle air conditioning control apparatus 100 detects a human body region from the acquired thermal image and detects a body part. The vehicle air conditioning control apparatus 100 may detect a distal part such as hands or ears where many shunt vessels suitable to determine thermal comfort are distributed, among various body parts. That is, the vehicle air conditioning control apparatus 100 may separate a distal part such as hands or ears from the human body region where a motion is captured, after removing a background from the acquired thermal image, using various algorithms.

In step S300, the vehicle air conditioning control apparatus 100 analyzes the skin temperature feature using a temperature of the human body region. That is, the vehicle air conditioning control apparatus 100 extracts body temperature information of the body part and extracts a feature of the skin temperature of the body part using the body temperature information. the scope of the feature of the skin temperature may include a feature vector of a skin temperature of the finger, a feature vector related to a temperature difference between the finger and the palm, a size of a specific frequency region in a frequency-converted thermal image information and a feature vector of a skin temperature of the ear. That is, the vehicle air conditioning control apparatus 100 detects a temperature for every part of the human body and extracts a skin temperature feature using the detected temperature. For example, the vehicle air conditioning control apparatus 100 extracts the skin temperature feature of the distal part such as hands or ears where many shunt vessels are distributed in the human body based on the detected body part and extracts the skin temperature of the body part in accordance with expansion or contraction of the shunt vessel.

In step S400, the vehicle air conditioning control apparatus 100 extracts the thermal comfort of each passenger based on a skin temperature feature analysis result. That is, the vehicle air conditioning control apparatus 100 estimates the thermal comfort of the human body through the analysis of the feature of the skin temperature and extracts the thermal comfort information based on the estimation. Further, the vehicle air conditioning control apparatus 100 may extract thermal comfort information in accordance with estimation. In the present embodiment, the thermal comfort may be extracted as numerical information. For example, a result of estimating the thermal comfort is thermal comfort information and may be extracted by number, like PMV, even though a predicted mean vote (PMV) is not directly calculated. As elements which affect the thermal comfort of the human body in the thermal environment, an air temperature in the vehicle, a mean radiant temperature (MRT), an air velocity, and a humidity are provided and as a personal element, a metabolism and do value are provided. However, it is complex to calculate the thermal comfort using the PMV for the space air conditioning and it is not easily permitted to accurately measure a factor required to calculate the thermal comfort with limited equipment. Therefore, a countermeasure to estimate the thermal comfort is necessary. Therefore, in the present embodiment, the thermal comfort felt by the human body may be estimated by the artificial intelligence model trained through learning using an artificial intelligence algorithm. That is, in the present embodiment, the vehicle air conditioning control apparatus 100 may acquire thermal comfort information of the passengers in the vehicle using one or more of a first deep neural network model and a second deep neural network model which are trained in advance to extract the thermal comfort of the human body by analyzing the skin temperature feature. In this case, the first deep neural network model may be trained to extract a skin temperature based on at least one of a finger skin temperature, a skin temperature difference between the finger and the palm, an ear skin temperature, and a size of a specific frequency region and acquire the thermal comfort information of the human body based on the skin temperature. Further, the second deep neural network model may be trained to extract a skin temperature based on at least one of thermal resistance information depending on the clothing wearing state of the passenger and temperature difference information in accordance with a position of a seat in the vehicle and acquire thermal comfort information of the human body based on the skin temperature.

In step S500, the vehicle air conditioning control apparatus 100 corrects the thermal comfort information of each passenger based on the vehicle information. That is, in the present embodiment, since it is characterized in the air conditioning is controlled in the vehicle, it is necessary to correct the thermal comfort in accordance with the characteristic of the vehicle. For example, when the window of the vehicle is open so that an event in the vehicle occurs, the vehicle air conditioning control apparatus 100 corrects the thermal comfort information by reflecting the distance from the air conditioning discharging port or a temperature of the seat. In this case, in the present embodiment, the vehicle air conditioning control apparatus 100 corrects the thermal comfort information of the passengers in the vehicle using a third deep neural network model which is trained in advance to analyze the vehicle information to extract a changed value of the thermal comfort information. In this case, the third deep neural network model may be trained to extract the changed value of the thermal comfort information of the human body based on at least one of vehicle internal environment sensing information, vehicle external environmental sensing information, and vehicle control sensing information and correct the thermal comfort information of the human body based on the changed value.

In step S600, the vehicle air conditioning control apparatus 100 identifies a thermal comfort index. That is, the vehicle air conditioning control apparatus 100 may acquire a numerical value of the thermal comfort corrected by reflecting the vehicle information to more easily control the air conditioning by more clearly distinguishes the thermal comfort of the passengers in the vehicle to easily control the air conditioning.

In step S700, the vehicle air conditioning control apparatus 100 detects a passenger having a thermal comfort index which is equal to or lower than a reference value, among the passengers. That is, the vehicle air conditioning control apparatus 100 may detect a passenger having a thermal comfort index which is equal to or lower than a reference value determined as dissatisfaction, among the passengers in the vehicle. In this case, the reference value may be initially set and may be changed.

In step S800, the vehicle air conditioning control apparatus 100 figures out an air conditioning discharging port located within a predetermined distance with respect to the passenger having a thermal comfort index which is equal to or lower than the reference value. That is, the vehicle air conditioning control apparatus 100 identifies a closest air conditioning discharging port with respect to the passenger having a thermal comfort index which is equal to or lower than the reference value. Further, the vehicle air conditioning control apparatus 100 identifies a plurality of air conditioning discharging ports which is located within a predetermined distance with respect to the passenger having a thermal comfort index which is equal to or lower than the reference value to influence on the passenger having a thermal comfort index which is equal to or lower than the reference value.

In step S900, the vehicle air conditioning control apparatus 100 adjusts a wind direction and a wind volume of the figured out air conditioning discharging port. That is, the vehicle air conditioning control apparatus 100 serves to control the operation of the air conditioner, for example, the temperature and the humidity of the air flow, a strength and a direction of the air flow, based on the extracted thermal comfort information of the human body. Therefore, the vehicle air conditioning control apparatus 100 may control the wind direction adjusting motor 150-1 and the wind volume adjusting motor 150-2 based on the thermal comfort information of the human body of each passenger. For example, when the human body feels cold or hot, the air conditioning may be controlled to control the temperature, the humidity, the strength and the direction of the air flow to raise or lower the temperature. That is, the vehicle air conditioning control apparatus 100 figures out an air conditioning discharging port located within a predetermined distance with respect to the passenger having a thermal comfort index which is equal to or lower than the reference value to adjust the wind volume based on the thermal comfort by the wind volume adjusting motor. Even though a wind discharging direction may be fixed by the selection of the user, the vehicle air conditioning control apparatus 100 may change the direction of the air discharging port through the wind direction adjusting motor to disperse the wind as a whole. In this case, the vehicle air conditioning control apparatus 100 may allow the discharging air flow to be directed to each passenger until the thermal comfort index of each passenger is equal to or higher than a predetermined value. Further, the vehicle air conditioning control apparatus 100 identifies a size of the change in the thermal comfort index of each passenger in real time to vary the strength and the direction of the air flow in accordance with a changed value.

Embodiments according to the present disclosure described above may be implemented in the form of computer programs that may be executed through various components on a computer, and such computer programs may be recorded in a computer-readable medium. Examples of the computer-readable media include, but are not limited to: magnetic media such as hard disks, floppy disks, and magnetic tape; optical media such as CD-ROM disks and DVD-ROM disks; magneto-optical media such as floptical disks; and hardware devices that are specially configured to store and execute program codes, such as ROM, RAM, and flash memory devices.

Meanwhile, the computer programs may be those specially designed and constructed for the purposes of the present disclosure or they may be of the kind well known and available to those skilled in the computer software arts. Examples of program code include both machine codes, such as produced by a compiler, and higher level code that may be executed by the computer using an interpreter.

As used in the present disclosure (especially in the appended claims), the singular forms "a," "an," and "the" include both singular and plural references, unless the context clearly states otherwise. Also, it should be understood that any numerical range recited herein is intended to include all sub-ranges subsumed therein (unless expressly indicated otherwise) and accordingly, the disclosed numeral ranges include every individual value between the minimum and maximum values of the numeral ranges.

Operations constituting the method of the present disclosure may be performed in appropriate order unless explicitly described in terms of order or described to the contrary. The present disclosure is not necessarily limited to the order of operations given in the description. All examples described herein or the terms indicative thereof ("for example," etc.) used herein are merely to describe the present disclosure in greater detail. Therefore, it should be understood that the scope of the present disclosure is not limited to the example embodiments described above or by the use of such terms unless limited by the appended claims. Therefore, it should be understood that the scope of the present disclosure is not limited to the example embodiments described above or by the use of such terms unless limited by the appended claims. Also, it should be apparent to those skilled in the art that various alterations, substitutions, and modifications may be made within the scope of the appended claims or equivalents thereof.

Therefore, technical ideas of the present disclosure are not limited to the above-mentioned embodiments, and it is intended that not only the appended claims, but also all changes equivalent to claims, should be considered to fall within the scope of the present disclosure.

What is claimed is:

1. A thermal comfort-based vehicle air conditioning control method, comprising:
   acquiring a thermal image in a vehicle using an image sensor;
   acquiring thermal comfort information of each passenger in the vehicle using the thermal image; and
   controlling air conditioning of the vehicle based on the thermal comfort information of each passenger,
   wherein the acquiring the thermal comfort information of each passenger in the vehicle using the thermal image includes:
   recognizing a body region of each passenger in the thermal image in the vehicle;
   analyzing a skin temperature using a temperature of the body region of each passenger and obtaining a skin temperature analysis result; and
   extracting thermal comfort of each passenger based on the skin temperature analysis result, and
   wherein the analyzing the skin temperature of each passenger further includes extracting the skin temperature based on a finger skin temperature and a skin temperature difference between a finger and a palm of the respective passenger.

2. The vehicle air conditioning control method according to claim 1, wherein the analyzing the skin temperature of each passenger further includes extracting the skin temperature of a body part within the body region having a plurality of shunt vessels.

3. The vehicle air conditioning control method according to claim 1, wherein the extracting the thermal comfort of each passenger based on the skin temperature analysis result further includes extracting the thermal comfort of each passenger using at least one of thermal resistance information in accordance with a clothing wearing state of each passenger and temperature difference information between different passengers in accordance with a seat position of each passenger in the vehicle.

4. The vehicle air conditioning control method according to claim 1, wherein the acquiring the thermal comfort information of each passenger in the vehicle using the thermal image includes:
  acquiring the thermal comfort information of each passenger in the vehicle using one or more of a first deep neural network model and a second deep neural network model,
  wherein the first and second deep neural network models are trained in advance to extract the thermal comfort of each passenger by analyzing the skin temperature of each passenger,
  wherein the first deep neural network model is a learning model trained to extract the skin temperature based on the finger skin temperature and the skin temperature difference between the finger and the palm of each passenger and acquire the thermal comfort information of each passenger based on the skin temperature, and
  wherein the second deep neural network model is a learning model trained to extract the skin temperature based on at least one of thermal resistance information based on the clothing wearing state of each passenger and temperature difference information in accordance with a seat position of each passenger in the vehicle and acquire thermal comfort information of each passenger based on the skin temperature.

5. The vehicle air conditioning control method according to claim 1, further comprising:
  acquiring vehicle information of the vehicle; and
  correcting the thermal comfort information of each passenger in the vehicle acquired using the thermal image, based on the vehicle information of the vehicle,
  wherein the vehicle information includes at least one of vehicle internal environment sensing information, vehicle external environment sensing information, and vehicle control sensing information.

6. The vehicle air conditioning control method according to claim 5, wherein the correcting the thermal comfort information of each passenger in the vehicle acquired using the thermal image, based on the vehicle information of the vehicle, includes:
  correcting the thermal comfort information of each passenger in the vehicle using a third deep neural network model trained in advance to extract a changed value of the thermal comfort information by analyzing the vehicle information of the vehicle, and
  wherein the third deep neural network model is a learning model trained to extract the changed value of the thermal comfort information of each passenger based on the at least one of vehicle internal environment sensing information, vehicle external environmental sensing information, and vehicle control sensing information and to correct the thermal comfort information of each passenger based on the changed value.

7. The vehicle air conditioning control method according to claim 1, wherein the controlling air conditioning of the vehicle based on the thermal comfort information of each passenger includes:
  identifying a thermal comfort index calculated based on the thermal comfort information of each passenger;
  detecting a first passenger having the thermal comfort index which is equal to or lower than a reference value among passengers in the vehicle;
  determining an air conditioning discharging port located within a predetermined distance from the first passenger; and
  adjusting a wind direction and a wind volume of the determined air conditioning discharging port.

8. The vehicle air conditioning control method according to claim 1, wherein the controlling air conditioning of the vehicle based on the thermal comfort information of each passenger includes:
  adjusting a wind direction of an air conditioning discharging port by controlling a discharging angle using a wind direction adjusting motor equipped in the air conditioning discharging port; and
  adjusting a wind volume of the air conditioning discharging port by calculating a target duty ratio by performing PID control and transmitting the calculated target duty ratio to a wind volume adjusting motor of the air conditioning discharging port, and
  wherein the adjusting the wind direction includes:
    calculating a gain value corresponding to the thermal comfort and using the calculated gain value as a gain value for the PID control.

9. A thermal comfort-based vehicle air conditioning control apparatus, comprising:
  a thermal image acquirer configured to acquire a thermal image in a vehicle using an image sensor;
  a thermal comfort acquirer configured to acquire thermal comfort information of each passenger in the vehicle using the thermal image; and
  a controller configured to control air conditioning of the vehicle based on the thermal comfort information of each passenger,
  wherein the thermal comfort acquirer includes:
  a body recognizer configured to recognize a body region of each passenger in the thermal image in the vehicle;
  an analyzer configured to analyze a skin temperature using a temperature of the body region of each passenger and obtaining a skin temperature analysis result; and
  an extractor configured to extract the thermal comfort of each passenger based on the skin temperature analysis result, and
  wherein the analyzer extracts the skin temperature based on a finger skin temperature and a skin temperature difference between a finger and a palm of the respective passenger.

10. The vehicle air conditioning control apparatus according claim 9, wherein the analyzer extracts, for each passenger, the skin temperature of a body part within the body region having a plurality of shunt vessels.

11. The vehicle air conditioning control apparatus according claim 9, wherein the extractor extracts the thermal comfort of each passenger using at least one of thermal resistance information in accordance with a clothing wearing state of each passenger and temperature difference information between different passengers in accordance with a seat position of each passenger in the vehicle.

12. The vehicle air conditioning control apparatus according to claim 9, wherein the thermal comfort acquirer acquires the thermal comfort information of each passenger in the vehicle using one or more of a first deep neural network model and a second deep neural network model,
  wherein the first and second deep neural network models are trained in advance to extract the thermal comfort of each passenger by analyzing the skin temperature of each passenger,
  wherein the first deep neural network model is a learning model trained to extract the skin temperature based on the finger skin temperature and the skin temperature difference between the finger and the palm of each passenger and acquire the thermal comfort information of each passenger based on the skin temperature, and wherein the second deep neural network model is a learning model trained to extract the skin temperature based on at least one of thermal resistance information based on the clothing wearing state of each passenger and temperature difference information in accordance with a seat position of each passenger in the vehicle and acquire the thermal comfort information of each passenger based on the skin temperature.

13. The vehicle air conditioning control apparatus according to claim 9, further comprising:

a vehicle information acquirer configured to acquire vehicle information of the vehicle; and a thermal comfort corrector configured to correct the thermal comfort information of each passenger in the vehicle acquired using the thermal image, based on the vehicle information of the vehicle, wherein the vehicle information includes at least one of vehicle internal environment sensing information, vehicle external environment sensing information, and vehicle control sensing information.

14. The vehicle air conditioning control apparatus according to claim 13, wherein the thermal comfort corrector corrects the thermal comfort information of each passenger in the vehicle using a third deep neural network model trained in advance to extract a changed value of the thermal comfort information by analyzing the vehicle information of the vehicle, and wherein the third deep neural network model is a learning model trained to extract the changed value of the thermal comfort information of each passenger based on the at least one of vehicle internal environment sensing information, vehicle external environmental sensing information, and vehicle control sensing information, and to correct the thermal comfort information of each passenger based on the changed value.

15. The vehicle air conditioning control apparatus according to claim 9, wherein the controller is further configured to:

detect a first passenger having a calculated thermal comfort index which is equal to or lower than a reference value among passengers in the vehicle based on the thermal comfort information of each passenger in the vehicle, determine an air conditioning discharging port located within a predetermined distance from the first passenger, and adjust a wind direction and a wind volume of the determined air conditioning discharging port.

16. The vehicle air conditioning control apparatus according to claim 9, wherein the controller is further configured to:

adjust a wind direction of an air conditioning discharging port by controlling a discharging angle using a wind direction adjusting motor equipped in the air conditioning discharging port, adjust a wind volume of the air conditioning discharging port by calculating a target duty ratio by performing PID control and transmitting the calculated target duty ratio to a wind volume adjusting motor of the air conditioning discharging port, calculate a gain value corresponding to the thermal comfort information, and adjust the wind volume using the calculated gain value as a gain value for the PID control.

* * * * *